United States Patent
Jain et al.

(10) Patent No.: US 6,979,740 B2
(45) Date of Patent: Dec. 27, 2005

(54) PROCESS FOR PREPARATION OF RING-SUBSTITUTED 8-AMINOQUINOLINE ANALOGS AS ANTIMALARIAL AGENTS

(75) Inventors: Rahul Jain, Punjab (IN); Meenakshi Jain, Punjab (IN); Prati Pal Singh, Punjab (IN); Sacita Singh, Punjab (IN); Sandeep Sachdeva, Punjab (IN); Vijai Misra, Punjab (IN); Poduri Ramarao, Punjab (IN); Chaman Lal Kaul, Punjab (IN); Kulbhushan Tikoo, Punjab (IN)

(73) Assignee: National Institute of Pharmaceutical Education and Research, Punjab (IN)

( * ) Notice: Subject to any disclaimer, the term of this patent is extended or adjusted under 35 U.S.C. 154(b) by 30 days.

(21) Appl. No.: 10/737,589

(22) Filed: Dec. 15, 2003

(65) Prior Publication Data

US 2004/0192724 A1 Sep. 30, 2004

(30) Foreign Application Priority Data

Mar. 27, 2003 (IN) .................................. 472/DEL/2003
Mar. 27, 2003 (IN) .................................. 459/DEL/2003

(51) Int. Cl.$^7$ ...................... C07D 215/38; A61K 31/47
(52) U.S. Cl. ...................................... 546/171; 514/311
(58) Field of Search .......................... 546/171; 514/311

(56) References Cited

U.S. PATENT DOCUMENTS 4,167,638 A * 9/1979 Chen et al. ................. 546/171
4,209,519 A * 6/1980 Kinnamon ................... 514/311

* cited by examiner

*Primary Examiner*—D. Margaret Seaman
(74) *Attorney, Agent, or Firm*—Rutan & Tucker, LLP

(57) ABSTRACT

The present invention is concerned with the development of novel 8-aminoquinoline analogs in the treatment and prevention of malaria and the said compound has broad spectrum of activity against the blood as well as tissue stages of the human malaria parasites makes these compounds very attractive in the cure and prevention of malaria caused by drug-sensitive and multidrug resistant strains and also it is expected that development of these compounds as ideal antimalarial agents may lead to suppression as well as radical cure of the malaria infection with single drug therapy.

28 Claims, No Drawings

PROCESS FOR PREPARATION OF RING-SUBSTITUTED 8-AMINOQUINOLINE ANALOGS AS ANTIMALARIAL AGENTS

FIELD OF THE INVENTION

The present invention is concerned with the development of novel 8-aminoquinoline analogs in the treatment and prevention of malaria and the said compound has broad spectrum of activity against the blood as well as tissue stages of the human malaria parasites that makes these compounds very attractive in the cure and prevention of malaria and also it is expected that development of these compounds as ideal antimalarial agents may lead to suppression as well as radical cure of the malaria infection with single drug therapy.

The present invention relates to a ring-substituted 8-aminoquinoline analogs and the preparation thereof which is useful as antimalarial agents. The present invention particularly relates to synthesis of 2-alkyl-4,5-disubstitited-6-methoxyprimaquine analogs having the formula 1, which are expected to offer an improved means for the chemotherapy of malaria.

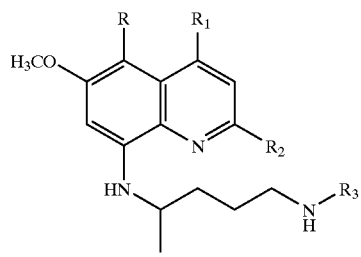

1

Where R represents H, straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups, $R_1$ represents H, $CH_3$, $C_2H_5$, $R_2$ represents straight chain alkyl group containing 1 to 5 carbons, branched alkyl groups, and cycloalkyl group containing 3 to 15 carbon atoms, $R_3$ represents various (R)- and (S)-amino acids or L-unnatural amino acids, and pharmacologically acceptable salts thereof, wherein the salt-forming acid may be organic or inorganic in nature. These 8-aminoquinoline class of compounds resulting from a unique and direct derivitazation at the C-2 position of the quinoline ring are expected to offer improvement over the existing chemotherapeutic approaches to malaria treatment by exerting their biological action on the parasite that may be present in the blood, tissues or blood and tissues of the host. It is expected that development of these compounds with such broad spectrum of activity as anti-malarial will lead to molecules which may provide single drug treatment for the suppression as well as radical cure for all species of human malaria infection.

BACKGROUND OF THE INVENTION

An infectious disease crisis of global proportion is today threatening health care system of many countries. Malaria, caused by protozoan belonging to the genus *Plasmodium*, is one of the most severe parasitic diseases. According to the World Health Organization (WHO) estimates, nearly four billion people, mostly in the tropical/impoverished countries, are at the risk of malaria. Each year 2–3 million people, mostly youngsters, in more than one hundred countries die from malaria, and its associated complications. Most malaria deaths occur in sub-Saharan Africa, where malaria accounts for one in five of all childhood deaths. Women are especially vulnerable during pregnancy. They are more likely to die from the disease, suffer miscarriages or give birth to premature, low-weight babies (Kevin, B. J. Drugs, 59, p 719, 2000). In India alone, 2.5–2.8 million clinical cases of malaria are reported annually. Civil conflicts, large-scale human migrations, climatic and environmental changes, inadequate and deteriorating health systems, growing insecticide and drug resistance have all combined to bring about the resurgence of malaria. Hence, malaria remains a major burden to human health in tropical and subtropical areas. The estimated global annual cost (in 1995) for malaria is about US $2 billion including that for loss of labor. However, ironically estimated annual expenditure on malaria research, prevention and treatment is approximately US $84 million, underlining the need for more efforts to combat this infectious disease.

The four identified species of the parasite responsible for causing human malaria are *Plasmodium falciparum, P. vivax, P. ovale* and *P. malariae*. However, *P. falciparum* and *P. vivax* account for more than 95% of malaria cases in the world, and *P. falciparum* causes most problems as a result of its prevalence, virulence and drug resistance, and nearly all deaths are attributed to this single parasitic species. Malaria infections caused by *P. falciparum* are prevalent in the major parts of Africa, sub-Saharan Africa and East Asian countries, whereas *P. vivax* is the causative species primarily of Indian sub-Continent. The disease can be treated in just 48 hours, yet it can cause fatal complications, if the diagnosis and treatment are delayed. Malaria is re-emerging as the biggest infectious killer and is currently the first priority tropical disease of the World Health Organization.

Life cycle of malaria parasite has various stages, and each stage has different degree of susceptibility to available antimalarial agents. The currently available antimalarial agents are conveniently divided into following two categories i.e. blood-schizontocidal antimalarial agents, which exert their biological activity against the erythrocytic asexual (blood) stages of the malaria parasite, and tissue-schizontocidal antimalarial agents, which exert their antimalarial action on the asexual exoerythrocytic (tissue) stages of the human malaria parasite. All of the available antimalarial drugs are losing their power to treat infection and have become inadequate for the treatment of malaria infection. *P. falciparum* has developed resistance against majority of blood-schizontocides such as chloroquine and mefloquine. On the other hand, available tissue-schizontocide such as primaquine is relatively ineffective against the blood schizonts. Additionally, the toxicity of primaquine requires it to be given in divided doses over 14 days to achieve radical curative effects in humans. These problems could be alleviated by the development of compounds, which, while retaining the tissue-schizontocidal activity of 8-aminoquinolines, have increased blood-schizontocidal activity comparable to that of chloroquine and mefloquine. This would enable single drug treatment for suppression as well as radical cure of the malaria infection. The logical lead compound for this research is primaquine and well supported by following observations: (1) 8-aminoquinolines is the only class of compounds proven to be successful for the treatment of relapsing malaria; (2) the 8-aminoquinolines, such as primaquine are easily synthesized and inexpensive to produce; (3) the 8-aminoquinolines, such as primaquine is the only drug available to exhibit activity against all the stages including that of blood- and tissue-stages of the human malaria life cycle; (4) the 8-aminoquinoline, primaquine has been shown to be effective against drug resistant strains of *P. falciparum*.

Despite research efforts of more than 60 years malaria is still one of the major killer of the world. Majority of people suffering from malaria belong to poorer section of society/countries, and are unable to afford expensive treatment. One of the factors for the development of resistance to the majority of drugs is believed to be the poor patient compliance. Therefore, elimination of expensive multi-drug therapies, with single drug will help in reducing the cost of treatment. This reduction in the cost would lead to more patient compliance. This would give better results in the prevention, spread and treatment of malaria.

OBJECTS OF THE INVENTION

The main object of the present invention is to provide a process for preparation of ring-substituted 8-aminoquinoline analogs.

Another main object of the present invention is to provide, 8-aminoquinoline analogs which exhibits superior antimalarial activities against drug-sensitive and multidrug-resistant parasites.

Another object of the present invention is to provide the ring substituted 8-aminoquinoline analogs having $LD_{50}$ value above 400 mg per body weight value.

Yet another object of the present invention is to provide the peptide derivatives of 8-aminoquinolines with reduced toxicity.

Another object of the present invention is to provide, 8-aminoquinoline analogs which exhibits reduced methemoglobin toxic side effects.

SUMMARY

The present invention relates to a ring-substituted 8-aminoquinoline analogs and their preparation thereof which is useful as antimalarial agents. The present invention particularly relates to synthesis of 2-alkyl-4,5-disubstitited-6-methoxyprimaquine analogs having the formula 1, which are expected to offer an improved means for the chemotherapy of malaria.

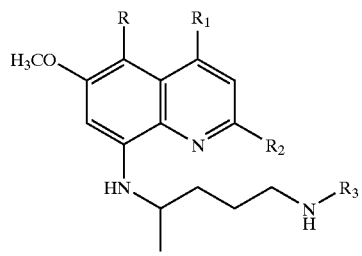

Where R represents H, straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups, $R_1$ represents H, $CH_3$, $C_2H_5$, $R_2$ represents straight chain alkyl group containing 1 to 5 carbons, branched alkyl groups, and cycloalkyl group containing 3 to 15 carbon atoms, $R_3$ represents various (R)- and (S)-amino acids or L-unnatural amino acids, and pharmacologically acceptable salts thereof, wherein the salt-forming acid may be organic or inorganic in nature. These 8-aminoquinoline class of compounds resulting from a unique and direct derivitazation at the C-2 position of the quinoline ring are expected to offer improvement over the existing chemotherapeutic approaches to malaria treatment by exerting their biological action on the parasite that may be present in the blood, tissues or blood and tissues of the host. It is expected that development of these compounds with such broad spectrum of activity as anti-malarial will lead to molecules which may provide single drug treatment for the suppression as well as radical cure for all species of human malaria infection.

DETAILED DESCRIPTION OF THE INVENTION

Accordingly the present invention relates to the development of novel 8-aminoquinoline analogs in the treatment and prevention of malaria and the broad spectrum of the activity against the blood as well as tissue stages of the human malaria parasites makes these compounds very attractive in the cure and prevention of malaria and also it is expected that development of these compounds as ideal antimalarial agents may lead to suppression as well as radical cure of the malaria infection with single drug therapy.

Accordingly, the ring-substituted 8-aminoquinoline analogs as of formula 1

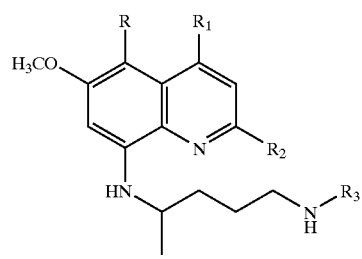

wherein R represents H; straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups, $R_1$ represents H, $CH_3$, $C_2H_5$, $R_2$ represents straight chain alkyl group containing 1 to 5 carbons, branched alkyl groups, and cycloalkyl group containing 3 to 15 carbon atoms, $R_3$ represents various (R)- and (S)-amino acids or L-unnatural amino acids.

In an embodiment of the present invention the ring substituted 8-aminoquinoline analogous as claimed in claim 1, wherein the value of R, R1, R2 and R3 of compound formula 1 are given below:

| R | $R_1$ | $R_2$ | $R_3$ |
|---|---|---|---|
| H | H | $C(CH_3)_3$ | H |
| c-$C_5H_9$ | H | H | H |
| H | H | 1-adamantyl | H |
| $CH(CH_3)_2$ | H | H | H |
| c-$C_6H_{11}$ | H | H | H |
| c-$C_5H_9$ | H | c-$C_5H_9$ | H |
| $CH(CH_3)_2$ | H | $CH(CH_3)_2$ | H |
| c-$C_6H_{11}$ | H | c-$C_6H_{11}$ | H |
| $OCH_3$ | H | $C(CH_3)_3$ | H |
| $OCH_3$ | H | c-$C_6H_{11}$ | H |
| $OCH_3$ | H | $CH(CH_3)_2$ | H |
| $OC_5H_{11}$ | $C_2H_5$ | $C(CH_3)_3$ | H |

-continued

| R | $R_1$ | $R_2$ | $R_3$ |
|---|---|---|---|
| $OC_8H_{17}$ | $C_2H_5$ | $C(CH_3)_3$ | H |
| $OCH_3$ | $CH_3$ | $C(CH_3)_3$ | H |
| H | H | $C(CH_3)_3$ | S-(Orn) |
| H | H | $C(CH_3)_3$ | S-(Val) |
| H | H | $C(CH_3)_3$ | S-(Lys) |
| H | H | $C(CH_3)_3$ | S-(Ala) |

In another embodiment of the present invention a ring substituted 8-aminoquinoline analogous wherein the compounds of formula 1 are active against *Plasmodium berghei* infection at a dose ranging between 10–100 mg for 4 days.

Yet in another embodiment of the present invention a ring substituted 8-aminoquinoline analogous wherein the compounds of formula 1 are active against *Plasmodiurn yoelii* infection at a dose ranging between 10–100 mg for 4 days.

Still in another embodiment of the present invention a ring substituted 8-aminoquinoline analogous wherein the $LD_{50}$ compounds of formula 1 is above 400 mg per kg of body weight.

Yet in another embodiment of the present invention a ring substituted 8-aminoquinoline analogous wherein the said analogous does not produces methemoglobin (MetHb) toxicity.

Yet in another embodiment of the present invention an anti-malarial composition a pharmaceutically effective amount of a ring substituted 8-aminoquinoline analogous wherein, the R represents H, straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups, $R_1$ represents H, $CH_3$, $C_2H_5$, $R_2$ represents straight chain alkyl group containing 1 to 5 carbons, branched alkyl groups, and cycloalkyl group containing 3 to 15 carbon atoms, $R_3$ represents various (R)- and (S)-amino acids or L-unnatural amino acids and pharmacologically acceptable additive(s).

Still in another embodiment of the present invention, wherein the pharmaceutically acceptable additives are acceptable diluents selected from group of a lactose, mannitol, sorbitol, microcrystalline cellulose, sucrose, sodium citrate, dicalcium phosphate, or any other ingredient of the similar nature alone or in a suitable combination thereof; binder selected from group of gum tragacanth, gum acacia, methyl cellulose, gelatin, polyvinyl pyrrolidone, starch or any other ingredient of the similar nature alone or in a suitable combination thereof; excipients selected from group of agar-agar, calcium carbonate, sodium carbonate, silicates, alginic acid, corn starch, potato tapioca starch, primogel or any other ingredient of the similar nature alone or in a suitable combination thereof; lubricants selected from group of a magnesium stearate, calcium stearate or steorotes, talc, solid polyethylene glycols, sodium lauryl sulphate or any other ingredient of the similar nature alone; wetting agents selected from group of acetyl alcohol, glyceryl monostearate or any other pharmaceutically acceptable flavor alone or in a suitable combination thereof; absorbents selected from group of kaolin, bentonite clay or any other pharmaceutically acceptable flavor alone or in a suitable combination thereof; retarding agents selected from group of wax, paraffin or any other pharmaceutically acceptable flavor alone or in a suitable combination thereof.

Yet in another embodiment of the present invention an anti-malarial composition, wherein the ring substituted 8-aminoquinoline analogous wherein the value of R, R1, R2 and R3 of compound formula 1 are given below:

| R | $R_1$ | $R_2$ | $R_3$ |
|---|---|---|---|
| H | H | $C(CH_3)_3$ | H |
| $c-C_5H_9$ | H | H | H |
| H | H | 1-adamantyl | H |
| $CH(CH_3)_2$ | H | H | H |
| $c-C_6H_{11}$ | H | H | H |
| $c-C_5H_9$ | H | $c-C_5H_9$ | H |
| $CH(CH_3)_2$ | H | $CH(CH_3)_2$ | H |
| $c-C_6H_{11}$ | H | $c-C_6H_{11}$ | H |
| $OCH_3$ | H | $C(CH_3)_3$ | H |
| $OCH_3$ | H | $c-C_6H_{11}$ | H |
| $OCH_3$ | H | $CH(CH_3)_2$ | H |
| $OC_5H_{11}$ | $C_2H_5$ | $C(CH_3)_3$ | H |
| $OC_8H_{17}$ | $C_2H_5$ | $C(CH_3)_3$ | H |
| $OCH_3$ | $CH_3$ | $C(CH_3)_3$ | H |
| H | H | $C(CH_3)_3$ | S-(Orn) |
| H | H | $C(CH_3)_3$ | S-(Val) |
| H | H | $C(CH_3)_3$ | S-(Lys) |
| H | H | $C(CH_3)_3$ | S-(Ala) |

Yet in another embodiment of the present invention an anti-malarial composition, wherein the said composition is having a broad spectrum of anti-malarial activity against blood stages, tissue stages of malarial parasite.

Still in another embodiment of the present invention an anti-malarial composition, wherein the said composition is effective against the resistant strains of human malarial parasite.

Yet in another embodiment of the present invention an anti-malarial composition, wherein the ring substituted 8-aminoquinoline analogous of formula 1 are active against *P. berghei* infection at a dose ranging between 10–100 mg for 4 days.

Yet in another embodiment of the present invention an anti-malarial composition, wherein the ring substituted 8-aminoquinoline analogous of formula 1 are active against *P. yoelii* infection at a dose ranging between 10–100 mg for 4 days.

Yet in another embodiment of the present invention an anti-malarial composition, wherein the $LD_{50}$ compounds of formula 1 is about 400 mg per kg of body weight. However, as the molecule is free of any toxicity a higher dose may be applied according to the degree of the malarial infection.

Still in another embodiment of the present invention an anti-malarial composition, wherein the ring substituted 8-aminoquinoline analogous of formula 1, said analogous does not produces methemoglobin (MetHb) toxicity.

Yet in another embodiment of the present invention a composition, wherein the composition is in the form of syrup/tablet/capsule/powder/injectables.

Accordingly, the present invention provides a process for preparation of ring-substituted 8-aminoquinoline analogs as of formula 1

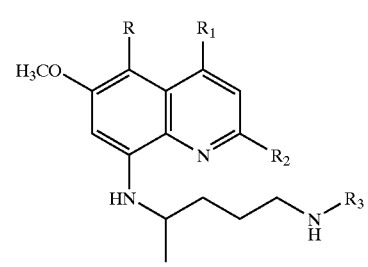

1 wherein R represents H, straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups, $R_1$ represents H, $CH_3$, $C_2H_5$, $R_2$ represents straight chain alkyl group containing 1 to 5 carbons, branched alkyl groups, and cycloalkyl group containing 3 to 15 carbon atoms, $R_3$ represents various (R)- and (S)-amino acids or L-unnatural amino acids, and pharmacologically acceptable salts thereof, wherein the salt-forming acid may be organic or inorganic in nature which comprises;

a. reacting 8-nitroquinolines with alkyl carboxylic acid in presence of sulphuric acid, silver nitrate and ammonium persulphate in aprotic solvent at reflux temperature for a period in the range of 5 min to 1 hr, isolating the ring substituted 8-nitroquinoline from the reaction mixture b. reducing the ring-substituted 8-nitroquinoline obtained in step (a) with a noble catalyst and hydrogen under pressure to give ring-substitued 8-aminoquinoline, c. reacting ring substituted 8-aminoquinoline with 2-(4-bromopentyl)-1,3-isoindolinedione and tryethylamine at a temperature ranging between 100–140 C for a period in the range of 3–21 hrs to provide isoindolinedione derivative, d. reacting the isoindolinedione derivative obtained in step (c) with hydrazine-hydrate in alcoholic solvent to give ring substituted N8-(4-amino-1-methylbutyl)-8-quinolinamine e. reacting N8-(4-amino-1-methylbutyl)-8-quinolinamine obtained in step (d) with N-protected amino acid and dicyclohexylcarbodimide in chloroalkane solvent at a temperature ranging between 10–50 C, isolating the ring substituted protective amino acid quinoline derivative followed by deprotection of amino acid moiety in the molecule to give compound of formula 1.

Still in another embodiment of the present invention, wherein the alkyl carboxylic acid is selected from a group consisting of tri-methyl acetic acid, isobutyric acid, cyclohexane carboxylic acid, 1-adamantanecarboxylic acid.

Still in another embodiment of the present invention, wherein 8-nitroquinoline is selected from 6-methoxy-8-nitroquinoline, 5,6-dimethoxy-8-nitroquinoline, 4-ethyl-5-pentoxy-6-methoxy-8-nitroquinoline, 4-ethyl-5-octoxy-6-methoxy-8-nitroquinoline, 4-methyl-5,6-dimethoxy-8-nitroquinoline.

Yet in another embodiment of the present invention, wherein the catalyst used for the reduction step (b) is raney-nickel.

Still in another embodiment of the present invention, wherein the reduction is carried out at a pressure in the range of 40–50 psi in a Parr hydrogenator.

Still in another embodiment of the present invention 16, wherein alcoholic solvent used is ethyl alcohol.

Still in another embodiment of the present invention, wherein the chloro-alkane solvent is selected from dichloromethane.

Still in another embodiment of the present invention, wherein the deprotection of benzyl-esters in amino acid moiety in the molecule in step (e) is carried out in presence of Pd-C in methanol in presence of hydrogen gas.

Yet in another embodiment of the present invention, wherein the deprotection of t-Boc protected amino acid is carried out in presence of methanolic HCl.

Still in another embodiment of the present invention, wherein the value of R, R1, R2 and R3 of formula 1 are given below:

| R | $R_1$ | $R_2$ | $R_3$ |
|---|---|---|---|
| H | H | $C(CH_3)_3$ | H |
| c-$C_5H_9$ | H | H | H |
| H | H | 1-adamantyl | H |
| $CH(CH_3)_2$ | H | H | H |
| c-$C_6H_{11}$ | H | H | H |
| c-$C_5H_9$ | H | c-$C_5H_9$ | H |
| $CH(CH_3)_2$ | H | $CH(CH_3)_2$ | H |
| c-$C_6H_{11}$ | H | c-$C_6H_{11}$ | H |
| $OCH_3$ | H | $C(CH_3)_3$ | H |
| $OCH_3$ | H | c-$C_6H_{11}$ | H |
| $OCH_3$ | H | $CH(CH_3)_2$ | H |
| $OC_5H_{11}$ | $C_2H_5$ | $C(CH_3)_3$ | H |
| $OC_8H_{17}$ | $C_2H_5$ | $C(CH_3)_3$ | H |
| $OCH_3$ | $CH_3$ | $C(CH_3)_3$ | H |
| H | H | $C(CH_3)_3$ | S-(Orn) |
| H | H | $C(CH_3)_3$ | S-(Val) |
| H | H | $C(CH_3)_3$ | S-(Lys) |
| H | H | $C(CH_3)_3$ | S-(Ala) |

Still in another embodiment of the present invention, wherein the compounds of formula 1 are active against *P. berghei, P. yoelii* infection at a dose ranging between 10–100 mg for 4 days.

Still in another embodiment of the present invention, wherein the $LD_{50}$ of compounds of formula 1 is in the range of 400 to 450 mg per kg of body weight.

Yet in another embodiment of the present invention, wherein the ring substituted 8-aminoquinoline analogous does not produces methemoglobin (MetHb) toxicity.

In another embodiment of the present invention A single drug method of treating a subject in need thereof by administrating pharmaceutically effective dosages of a ring substituted 8-aminoquinoline analogous of formula 1 as defined in claim 1 along with a pharmaceutically acceptable salt(s), carrier or additives to the mammals.

Still in another embodiment of the present invention the subject is mammals and preferably humans.

Still in another embodiment of the present invention, wherein the compounds of formula 1 are active against *P. berghei* and *P. yoelii* infection at a dose ranging between 10–100 mg for 4 days.

Still in another embodiment of the present invention, wherein the $LD_{50}$ of compounds of formula 1 is in the range of 400 to 450 mg per kg of body weight.

Still in another embodiment of the present invention, wherein the said composition is having a broad spectrum of anti-malarial activity against blood stages, tissue stages of malarial parasite.

Yet in another embodiment of the present invention, wherein the said composition is effective against the resistant strains of human malarial parasite.

Most of the available antimalarial drugs are incapable and ineffectual for the treatment of malaria infection. Development of resistance by *P. falciparum* has been documented against majority of blood-schizontocides. Furthermore, available tissue-schizontocides are highly toxic for human use as causal prophylactics and gametocytocides.

Primaquine, $N^8$-(4-amino-1-methylbutyl)-6-methoxy-8-quinolinamine, is highly effective tissue-schizontocidal agent, and has direct and fast gametocytocidal action on all species of malarial parasite. The drug also has blood-schizontocidal activity but only at dangerously toxic doses for human use. Its high toxicity profile [methemoglobinemia and hemolysis particularly in individuals who are genetically deficient of glucose-6-phosphate dehydrogenase (G-6PD)] has largely deterred clinician from its safer use.

Our attention was drawn to a recent publication (LaMontagne, M P., Blumbergs, P., Smith D. C. J. Med. Chem. 32, p 1728, 1989), where placement of a methoxy group at the C-2 position of the quinoline ring in a primaquine derivative produced an analogue far superior with exceptional tissue- and blood-schizontocidal activities. There are three earlier reports on the synthesis of 2-substituted primaquine derivatives [Shetty, R. V., Wetter, W. P., Blanton, C. D. J. Med. Chem. 20, p 1349, 1977, where substitution at C-2 position are various benzyloxy and benzylthio groups], [Shetty, R. V., Blanton, C. D. J. Med. Chem. 21, p 995, 1978, where substitution at C-2 position are $CH_2C_6H_5$, $OCH_3$, $NH_2$, $N(CH_3)_3$ Cl, $C_2H_5$, $CH=CH_2$, $NHCOCH_3$] and [Carroll, F. I, Berrang, B. D., Linn, C. P. J. Med. Chem. 23, p 581, 1980, where substitution at C-2 position are $C_2H_5$, $CH=CH_2$, $CH_3$, $CH_2CH_2Br$). However, none of these compounds exhibited superior biological activities.

The present invention describes the utilization of a radical homolytic free radical reaction [Scheme 1] to provide novel 2-alkyl-8-aminoquinoline, 5-alkyl-8-aminoquinoline and 2,5-dialkyl-8-aminoquinoline derivatives and the surprisingly strong broad-spectrum antimalarial activities of the analogs belonging to 2-alkyl-8-aminoquinoline series.

ring, which prevents the biotransformation to inactive and phototoxic 1H-2-oxoquinolines. To our surprise, no such metabolic pathway is known for primaquine; though, introduction of 2-alkoxy (LaMontagane, M. P., Blumberg, P., Smith, D. C. J. Med. Chem. 1989, 32, 1728–1732) and 2-alkyl (Schmidt, L. H. Antimicrob. Agents Chemother. 1983, 24, 615–652) substituents in the primaquine led to an overall increase in therapeutic efficacy. Whether, these compounds show improved efficacy by blocking the proposed metabolic pathway, is yet uncertain. Based upon these observations, we hypothesize that the placement of a metabolically stable bulky alkyl group at the C-2 position of the quinoline ring in primaquine may produce analogs with improved therapeutic efficacies due to their inability to undergo C-2 position metabolic pathway described for the quinoline ring.

The requisite 8-nitroquinolines required for the synthesis of ring-substituted-8-nitroquinolines (Scheme 1) are synthesized from appropriate nitroanilines by Skraup synthesis following the procedures reported earlier (Jain, R., Jain, S., Gupta, R. C., Anand, N., Dutta, G. P. and Puri, S. K. Ind. J. Chem. 33B, p 251, 1994; Vangapandu, S., Sachdeva, S., Jain, M, Singh, S., Singh, P. P., Kaul, C. L., Jain, R. Bioorg. Med. Chem. 2003, 11, 4557–4568).

Scheme 1

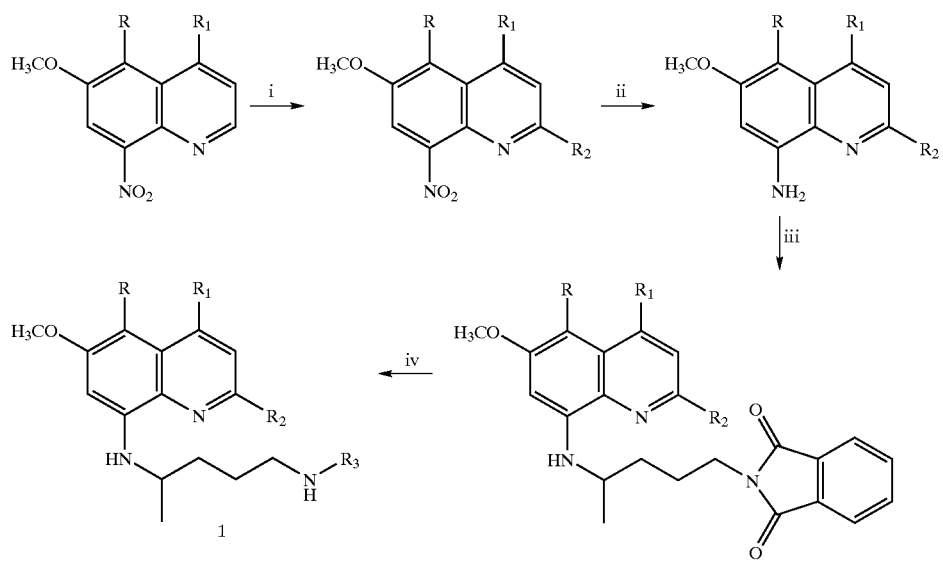

i. $R_2CO_2H$, $AgNO_3$, $(NH_4)_2S_2O_8$, 10% $H_2SO_4/CH_3CN$;
ii. raney-Ni/$H_2$;
iii. 2-(4-bromopentyl)-1,3-isoindolinedione, $Et_3N$;
iv. (a) $NH_2NH_2$, EtOH, (b) Boc/Z-AA-OH, DCC, (c) MeOH/HCl or Pd——C, $H_2$, RTP The rationale for the synthesis of these compound is as follows: One of the main metabolic degradation pathways known for the quinoline moiety results in oxidative biotransformation at the C-2 position, and converts it to 1H-2-oxoquinoline. This pathway is supported by the recent studies conducted by Mirghani and coworkers (Mirghani R. A., Ericsson O., Cook J., Yu P., Gustafsson L. L. J. Chromatogr. B Biomed. Sci. Appl. 2001, 754, 57–64) that identified 2-quininone (known to display phototoxic side-effects) as one of the major metabolite of quinine. Furthermore, high antimalarial activity associated with mefloquine and related compounds is known to be derived by the placement of a trifluoromethyl group at the C-2 position of the quinoline 8-Nitroquinolines on silver catalyzed radical oxidative decarboxylation of alkylcarboxylic acids by ammonium persulfate in 10% $H_2SO_4$ as solvent based upon the procedures reported by us earlier for ring-substituted bioimidazoles (Jain, R., Cohen, L. A. King, M. M., El-Kadi, N. Tetrahedron, 53, p2365, 1997, Tetrahedron, 53, p4539, 1997) led to a unique homolytic free radical initiated direct ring alkylation, and readily provided mono and dialkylated 8-nitroquinolines in 60–65% yield. $N^8$-(4-amino-1-methylbutyl)-2-alkyl-6-methoxy-8-quinolinamine derivatives (1, $R_3$=H), $N^8$-(4-amino-1-methylbutyl)-5-alkyl-6-methoxy-8-quinolinamine (1, $R_3$=H) and $N^8$-(4-amino-1-methylbutyl)-2,5-dialkyl-6-methoxy-8-quinolinamine derivatives (1, $R_3$=H) were synthesized from appropriate 2-alkyl/5-alkyl/2,5-dialkyl-6-methoxy-8-nitroquinoline derivatives in three steps following the procedures reported earlier (Jain, R., Jain, S., Gupta, R. C., Anand, N., Dutta, G. P. and Puri, S. K. Ind. J. Chem. 33B, p 251, 1994; Vangapandu, S., Sachdeva, S., Jain, M, Singh, S., Singh, P. P., Kaul, C. L., Jain, R. Bioorg. Med. Chem. 2003, 11, 4557–4568).

Primaquine is known to have poor pharmacokinetic properties. Furthermore, the drug has a short half-life (4–6 h), low therapeutic index and high toxicity, which are the limiting factors in its use as an ideal drug. These limitations can be modified by a prodrug approach, which involves appropriate chemical modification of the drug. A prodrug is a pharmacologically inactive derivative of a parent drug molecule that requires spontaneous or enzymatic transformation within the body in order to release the active drug that may also have improved biological properties over the parent drug molecule. It has, in fact, been shown that linking the primaquine to small peptides resulted in the formation of compounds, which possess reduced toxicity and a longer half-life compared to primaquine. Furthermore, we have earlier demonstrated that linking amino acids to the side chain amino group at C-8 position of the quinoline ring is found to increase the biological activity with reduced toxicity (Jain, R., Jain, S., Gupta, R. C., Anand, N., Dutta, G. P. and Puri, S. K. Ind. J. Chem. 33B, p 251, 1994; Hofsteenge, J., Capuano, A., Altszuler, R.; Moore, S. J. Med. Chem. 29, p 1765, 1986, Philip, A., Kepler, J. A., Johnson, B. H., Carroll, F. I. J. Med. Chem. 31, p 870, 1988). Therefore, a variety of amino acid derivatives of ring-substituted primaquine derivatives as their putative prodrugs were also synthesized. Thus, 8-aminoquinolines compounds (1, $R_3$=H) on reaction with Z- or Boc-protected amino acids in the presence of 1,3-dicyclohexylcarbodiimide (DCC) in anhydrous dichloromethane afforded the protected compounds in quantitative yield. Removal of protective group either by catalytic hydrogenation in the presence of 10% Pd—C or acid hydrolysis as in the case of Boc-group provided the ring-substituted $N^1$-[4-(6-methoxy/5-alkoxy-6-methoxy/-4-alkyl-8-quinolylamino)pentyl]-2-amino-2-substituted acetamides [1, $R_3$=various (R)- and (S)-amino acids, L-unnatural amino acids] in quantitative yield.

Accordingly, the present invention provides a process for preparation of ring-substituted 8-aminoquinoline analogs as of formula 1

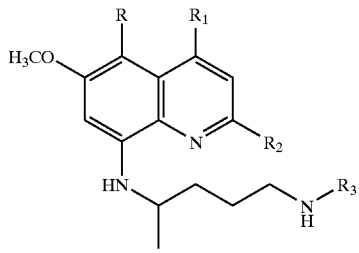

1 wherein R represents H, straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups, $R_1$ represents H, $CH_3$, $C_2H_5$, $R_2$ represents straight chain alkyl group containing 1 to 5 carbons, branched alkyl groups, and cycloalkyl group containing 3 to 15 carbon atoms, $R_3$ represents various (R)- and (S)-amino acids or L-unnatural amino acids, and pharmacologically acceptable salts thereof, wherein the salt-forming acid may be organic or inorganic in nature which comprises;

a. reacting 8-nitroquinolines with alkyl carboxylic acid in presence of sulphuric acid, silver nitrate and ammonium persulphate in aprotic solvent at reflux temperature for a period in the range of 5 min to 1 hr, isolating the ring substituted 8-nitroquinoline from the reaction mixture b. reducing the ring-substituted 8-nitroquinoline obtained in step (a) with a noble catalyst and hydrogen under pressure to give ring-substitued 8-aminoquinoline, c. reacting ring substituted 8-aminoquinoline with 2-(4-bromopentyl)-1,3-isoindolinedione and tryethylamine at a temperature ranging between 100–140 C for a period in the range of 3–8 hrs to provide isoindolinedione derivative, d. reacting the isoindolinedione derivative obtained in step (c) with hydrazine-hydrate in alcoholic solvent to give ring substituted N8-(4-amino-1-methylbutyl)-8-quinolinamine e. reacting N8-(4-amino-1-methylbutyl)-8-quinolinamine obtained in step (d) with N-protected amino acid and dicyclohexylcarbodiimide in chloroalkane solvent at a temperature ranging between 10–50 C, isolating the ring substituted protective amino acid quinoline derivative followed by deprotection of amino acid moiety in the molecule to give compound of formula 1.

In an embodiment of the present invention the alkyl carboxylic acid is selected from a group consisting of tri-methyl acetic acid, isobutyric acid, cyclo-hexane carboxylic acid, 1-adamantanecarboxylic acid.

In another embodiment of the present invention 8-nitroquinoline is selected from 6-methoxy-8-nitroquinoline, 5,6-dimethoxy-8-nitroquinoline, 4-ethyl-5-pentoxy-6-methoxy-8-nitroquinoline, 4-ethyl-5-octoxy-6-methoxy-8-nitroquinoline, 4-methyl-5,6-dimethoxy-8-nitroquinoline, In yet another embodiment of the present invention the catalyst used for the reduction step (b) is raney-nickel.

In yet another embodiment of the present invention the reduction is carried out at a pressure in the range of 40–50 psi in a Parr hydrogenator.

In yet another embodiment of the present invention alcoholic solvent used is ethyl alcohol.

In yet another embodiment of the present invention the chloro-alkane solvent is selected from dichloro-methane.

In another embodiment of the present invention the deprotection of bezyl-esters in amino, acid moiety in the molecule in step (e) is carried out in presence of Pd—C in methanol in presence of hydrogen gas.

In yet another embodiment of the present invention the deprotection of t-Boc protected amino acid is carried out in presence of methanolic HCl.

In yet another embodiment of the present invention the compounds of formula 1 are active in mice against P. berghei, P. yoelii infection at a dose ranging between 10–100 mg for 4 days.

In yet another embodiment of the present invention the $LD_{50}$ compounds of formula 1 is above 400 mg per kg of body weight.

Brief Description of the Tables

Table 1: In vivo blood-schizontocidal activity of compounds against P. berghei infection in mice Table 2: In vivo blood-schizontocidal activity of compounds against chloroquine and mefloquine drug-resistant P. yoelii nigeriensis strain in mice Table 3: Acute toxicity studies in Swiss Mice (5, 50, 150, 450 mg/kg)

Table 4: A comparison of methanoglobin toxicity between commonly used primaquine drug and 2-tert-Butylprimaquine Table 5: In vitro antimalarial data of 2-tert-butylprimaquine against P. falciparum

Biological Activity

Blood schizontocidal activity evaluation of potential antimalarial compounds against *Plasmodium berghei* (sensitive strain) and *P. yoelii* nigeriensis (resistant strain) infection in mice.

Test Procedure: On day '0', groups of 6 mice each were inoculated, intraperitoneally, with $1 \times 10^7$ infected-erythrocytes, from a donor mouse. Four hours later, mice were administered test compounds/chloroquine primaquine/vehicle, orally. A total of 4 doses were given on days D'0', D+1, D+2, and D+3. The tail blood smears were made on day D+4 and D+7, stained with Geimsa, and examined microscopically. The minimum dose which completely suppressed parasitaemia on days D+4 and D+7 was designated "minimum effective dose (MED)" or "suppressive dose" and, the minimum dose, which cleared the parasitaemia for up to 28 days, was termed "curative dose". The results of blood-schizontocidal activities for the synthesized compounds are given below in Table 1.

TABLE 1

| R | $R_1$ | $R_2$ | $R_3$ | Biological activity at (mg/kg/days × 4) |
|---|---|---|---|---|
| H | H | $C(CH_3)_3$ | H | Curative at 10 mg/kg |
| c-$C_5H_9$ | H | H | H | Inactive at 100 mg/kg |
| H | H | 1-adamantyl | H | Inactive at 100 mg/kg |
| $CH(CH_3)_2$ | H | H | H | Inactive at 100 mg/kg |
| c-$C_6H_{11}$ | H | H | H | Inactive at 100 mg/kg |
| c-$C_5H_9$ | H | c-$C_5H_9$ | H | Inactive at 100 mg/kg |
| $CH(CH_3)_2$ | H | $CH(CH_3)_2$ | H | Inactive at 100 mg/kg |
| c-$C_6H_{11}$ | H | c-$C_6H_{11}$ | H | Inactive at 100 mg/kg |
| $OCH_3$ | H | $C(CH_3)_3$ | H | Inactive at 100 mg/kg |
| $OCH_3$ | H | c-$C_6H_{11}$ | H | Inactive at 100 mg/kg |
| $OCH_3$ | H | $CH(CH_3)_2$ | H | Inactive at 100 mg/kg |
| $OC_5H_{11}$ | $C_2H_5$ | $C(CH_3)_3$ | H | Curative at 100 mg/kg |
| $OC_8H_{17}$ | $C_2H_5$ | $C(CH_3)_3$ | H | Curative at 100 mg/kg |
| $OCH_3$ | $CH_3$ | $C(CH_3)_3$ | H | Curative at 100 mg/kg |
| H | H | $C(CH_3)_3$ | S-(Orn) | Curative at 100 mg/kg |
| H | H | $C(CH_3)_3$ | S-(Val) | Inactive at 100 mg/kg |
| H | H | $C(CH_3)_3$ | S-(Lys) | Suppressive at 10 mg/kg |
| H | H | $C(CH_3)_3$ | S-(Ala) | Suppressive at 10 mg/kg |

*Standard drug chloroquine has suppressive activity at 8 mg/kg, and curative activity at 12 mg/kg As evident from Table 1, the most effective compound of the series 1 [R=$R_1$=$R_3$=H, $R_2$=$C(CH_3)_3$] is curative at a dose of 10 mg/kg in *P. berghei* infected mice model thereby indicating its superiority over chloroquine in this test model. On the other hand, compounds (12–15, 17–18) were found to be curative at the initial tested dose of 100 mg/kg in *P. berghei* infected mice model. Further screening of compounds (17–18) indicated them to have suppressive activity at 10 mg/kg *P. berghei* infected mice model.

Compound (1) found curative at 10 mg/kg against *P. berghei* infected mice model was then tested against chloroquine and mefloquine drug-resistant *P. yoelii* nigeriensis (multidrug resistant strain) in mice at various dosage and results are summarized in Table 2.

TABLE 2

| R | $R_1$ | $R_2$ | $R_3$ | Biological activity at (mg/kg/days × 4) |
|---|---|---|---|---|
| H | H | $C(CH_3)_3$ | H | Curative at 100 mg/kg |
| | | | | Curative at 50 mg/kg |
| | | | | Curative at 25 mg/kg |
| | | | | Suppressive at 10 mg/kg |

The most effective compound 1 [R=$R_1$=$R_3$=H, $R_2$=$C(CH_3)_3$] of the series was further evaluated for acute toxicity studies in Swiss mice. A group of ten mice with equal ratio of male and female were subjected to a single dose of 5, 50, 150 and 450 mg/kg. The compounds were evaluated for acute toxicity as per the protocols of Schedule 'Y" of Drug and Cosmetic Act, 1988, Govt. of India, Ministry of Health and Family Welfare, except the number of animals used in the present investigation and results are as given in Table 3 indicates that compound is completely safe at 50 mg/kg.

TABLE 3

| Compound | Dose | % Mortality Female | % Mortality Male | % Mortality Total |
|---|---|---|---|---|
| [R=$R_1$=$R_3$=H, | 5 mg/kg | 0 | 0 | 0 |
| $R_2$=$C(CH_3)_3$] | 50 mg/kg | 0 | 0 | 0 |
| | 150 mg/kg | 0 | 0 | 0 |
| | 450 mg/kg | 0 | 0 | 0 |

The pronounced activity of 1 [R=$R_1$=$R_3$=H, $R_2$=$C(CH_3)_3$] against the chloroquine, mefloquine and quinine resistant strain of *P. yoelii nigeriensis* has made this compound a very attractive molecule for clinical drug development. Since, the basic sub-structure in our study is primaquine (clinically used radical curative drug), thus we anticipate observing the same (as primaquine) or increased degree of tissue-schizontocidal activity of this molecule. It is expected that this unique blend of broad-spectrum of antimalarial activity against blood stages, tissue stages, and resistant strains of the human malaria parasites may make these compounds very attractive in the cure and prevention of malaria. It is further expected that the development of these compounds may offer the possibility of a single drug that can cure all of the relapsing and non-relapsing forms of malaria.

Reduced Methemoglobin Toxicity

The most effective compound was further subjected to methemoglobin toxicity studies. The protocol used is as follows: In vivo MetHb-inducing properties estimation was carried out in Mastomys coucha, a rapid rodent animal model using protocols reported earlier (Srivastava, P., Singh, S., Jain, G. K., Puri, S. K., Pandey, V. C. *Ecotox. Environ. Safety*. 2000, 45, 236–239). Briefly; six animals per group of both sexes, 2–3 months old and body weight between 40–50 g were used for the present investigation. Drug was administered intraperitoneally (ip) or orally at various dosage for single day/three consecutive days. Primaquine is used as the standard drug for the test. It is known that primaquine is readily absorbed from the gastro-intestinal tract and peak plasma concentration reaches within 3 h and falls within an apparent elimination half time of 6 h. Keeping the above pharmacokinetic profile in mind, the blood samples were collected after 4 h of drug administration and % increase in MetHb was calculated.

The significant results are obtained from methemoglobin toxicity conducted on the most effective analogue from the series [Example 43: $N^8$-(4-Amino-1-methylbutyl)-2-tert-butyl-6-methoxy-8-quinolinamine]. The 8-quinolinamine class of compounds that includes primaquine produces substantial amount of methemoglobin (MetHb), and is one of the main toxic side effect of this class. It was found that this compound [Example 43: $N^8$-(4-Amino-1-methylbutyl)-2-tert-butyl-6-methoxy-8-quinolinamine OR it can be called as 2-tert-butylprimaquine)] is completely devoid of this toxic manifestation in vivo. This is the first potent 8-quinolinamine discovered without MetHb toxicity, and thus is extremely important finding. A comparative study with commonly used standard drug (Primaquine) for methanoglobin toxicity is given in Table 4.

TABLE 4

| Compounds | Dose Protocol | | | |
|---|---|---|---|---|
| | 15 mg/kg/day x 4 days (oral) | 50 mg/kg (single dose) (oral) | 15 mg/kg/day x 4 days (ip) | 50 mg/kg (single dose) (ip) |
| | (%) Methemoglobin (MetHb) Increase | | | |
| 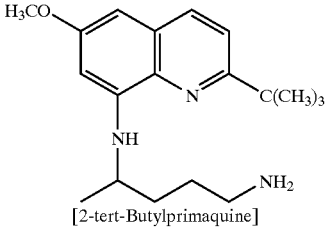 [2-tert-Butylprimaquine] | 0% | 0% | 0% | 0% |
| 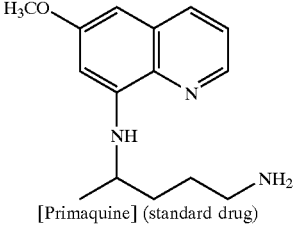 [Primaquine] (standard drug) | 3.57% | 2.58% | 3.38% | 3.38% |
| Control | 0% | 0% | 0% | 0% |

In Vitro Antimalarial Activity Against *P. falciparum*

Protocol: Different drug dilutions [test compounds and chloroquine (positive control)] were prepared in complete RPMI (medium RPMI 1640+10% AB⁺ human serum; CRPMI). Fifty μL of each dilution was transferred to the respective well of a microtiter plate in triplicates. Parasitized erythrocytes (PE; mainly rings; 4% parasitaemia; 5% hematokrit) were added to each well. Volume in each well was made up to 200 μL with CRPMI. The plates were incubated at 37° C. in a candle jar. After 24–48 h of incubation, thin smears from each well were made and stained with Giemsa. The number of PE/10,000 cells was counted. Percent inhibition by the drug over the control (well which does not contain any drug) was plotted against the respective logarithmic concentration of the drug. Using non-linear regression analysis, the $IC_{50}$ of the test compounds was then calculated.

TABLE 5

| Compounds | *P. falciparum* $(IC_{50})^a$ |
|---|---|
| 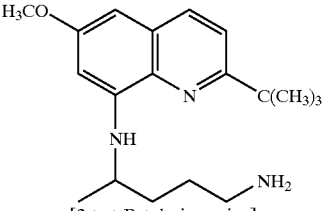 [2-tert-Butylprimaquine] | 39.06 ng |

TABLE 5-continued

| Compounds | *P. falciparum* $(IC_{50})^a$ |
|---|---|
| 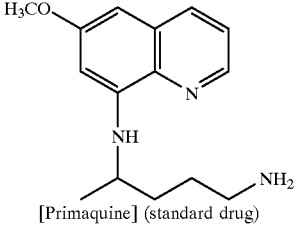 [Primaquine] (standard drug) | Not active |
| 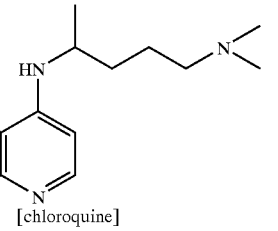 [chloroquine] | 113 ng/mL |

EXAMPLES

The following examples are given by way of illustration and should not construed the scope of the invention.

Example 1

Synthesis of 2-tert-Butyl-6-methoxy-8-nitroquinoline
6-Methoxy-8-nitroquinoline (1 mmol) (scheme 1) was dissolved in CH₃CN (5 mL) while reaction mixture was warmed to 70° C. Silver nitrate (0.6 mmol), trimethylacetic acid (2.5 mmol), and 10% $H_2SO_4$ (10 mL) was then added to the reaction mixture. A freshly prepared solution of ammonium persulfate (3 mmol) in water (10 mL) was added drop wise to the pre-heated (70° C.) mixture during 10 minutes. The heating source was then removed and reaction proceeded with evolution of carbon dioxide. After 10 minutes, reaction mixture was poured onto ice, and resulting mixture was made alkaline with addition of 30% $NH_4OH$. Extracted with ethyl acetate (4×50 mL), and combined extracts were washed with NaCl solution (2×10 mL). Dried over $Na_2SO_4$ and solvent removed in vacuo to afford oil, which on flash column chromatography over silica gel (230–400 mesh) gave 2-tert-Butyl-6-methoxy-8-nitroquinoline in good yield.

Yield: 62%; IR (KBr): 1529 and 1362 cm$^{-1}$ ($NO_2$); $^1$H NMR (CDCl$_3$): δ 8.03 (d, 1H, 4-Ar—H, J=8.7 Hz), 7.62 (d, 1H, 3-Ar—H, J=2.7 Hz), 7.58 (d, 1H, 7-Ar—H, J=8.8 Hz), 7.23 (d, 1H, 5-Ar—H, J=2.5 Hz), 3.96 (s, 3H, OCH$_3$), 1.41 (s, 9H, 3×CH$_3$) $^{13}$C NMR (CDCl$_3$): δ 155.5, 134.65, 128.10, 120.2, 115.4, 109.1, 56.1, 38.3, 29.8; MS (EI): m/z 260 (M$^+$).

Examples listed below are prepared using the protocol described above and by reacting 5,6-dimethoxy-8-nitroquinolines with trimethylacetic acid, cyclohexanecarboxylic acid and isobutyric acid respectively.

Example 2

2-tert-Butyl-5,6-dimethoxy-8-nitroquinoline

Yield: 65%; IR (KBr): 1528 cm$^{-1}$ and 1349 cm$^{-1}$ ($NO_2$); $^1$H NMR (CDCl$_3$): δ 8.05 (d, 1H, 4-Ar—H, J=9 Hz), 7.89 (s, 1H, 7-Ar—H), 7.60 (d, 1H, 3-Ar—H, J=9 Hz), 4.07 (s, 3H, 5-OCH$_3$), 4.02 (s, 3H, 6-OCH$_3$), 1.42 (s, 9H, 3×CH$_3$); HRMS (ESI): 291.2 (M+1).

Example 3

2-Cyclohexyl-5,6-dimethoxy-8-nitroquinoline

Yield: 57%; IR (KBr): 1540 and 1375 cm$^{-1}$ ($NO_2$); $^1$H NMR (CDCl$_3$): δ 7.94 (d, 1H, 4-Ar—H, J=9 Hz), 7.75 (s, 1H, 7-Ar—H), 6.93 (d, 1H, 3-Ar—H, J=9 Hz), 3.98 (s, 3H, 5-OCH$_3$), 3.97 (s, 3H, 6-OCH$_3$), 2.92 (m, 1H, CH), 1.25 (s, 10H, 5×CH$_2$); MS (EI): m/z 316 (M$^+$).

Example 4

2-Isopropyl-5,6-dimethoxy-8-nitroquinoline

Yield: 55%; IR (KBr): 1565 and 1340 cm$^{-1}$ ($NO_2$); $^1$H NMR (CDCl$_3$): δ 7.87 (dd, 1H, 4-Ar—H, J=8.9 Hz), 7.65 (s, 1H, 7-Ar—H), 6.86 (d, 1H, 3-Ar—H, J=8.9 Hz), 4.08 (s, 3H, 5-OCH$_3$), 4.02 (s, 3H, 6-OCH$_3$), 3.12 (m, 1H, CH), 1.25 (s, 6H, 2×CH$_3$), MS (EI): m/z 276 (M$^+$).

Example 5

2-tert-Butyl-4-ethyl-5-pentoxy-6-methoxy-8-nitroquinoline

This compound was synthesized using above-mentioned procedure and 4-ethyl-5-pentoxy-6-methoxy-8-nitroquinoline as the starting material in the presence of trimethyl acetic acid.

Yield: 42%; IR (KBr): 1550, 1345 cm$^{-1}$ ($NO_2$); $^1$H NMR (CDCl$_3$): δ 7.47 (s, 1H, 7-Ar—H), 7.18 (s, 1H, 3-Ar—H), 4.03 (t, 2H, OCH$_2$), 3.90 (s, 3H, OCH$_3$), 3.18 (q, 2H, CH$_2$), 1.80 (m, 4H, 2×CH$_2$), 1.33 (m, 2H, CH$_2$), 1.32 (s, 3H, 3×CH$_3$), 0.82 (t, 3H, CH$_3$); MS (APCI): m/z 375 (M+1).

Example 6

2-tert-Butyl-4-ethyl-5-octoxy-6-methoxy-8-nitroquinoline

This compound was synthesized using above-mentioned procedure and 4-ethyl-5-octoxy-6-methoxy-8-nitroquinoline as the starting material in the presence of trimethylacetic acid.

Yield: 35%; IR (KBr): 1522 and 1345 cm$^{-1}$ ($NO_2$); $^1$H NMR (CDCl$_3$): δ 7.75 (s, 1H, 7-Ar—H), 7.33 (s, 1H, 3-Ar—H), 4.10 (t, 2H, OCH$_2$), 3.98 (s, 3H, OCH$_3$), 3.25 (q, 2H, CH$_2$), 1.64 (m, 2H, CH$_2$), 1.52 (m, 6H, 3×CH$_2$), 1.31 (s, 9H, 3×CH$_3$), 0.88 (t, 3H, CH$_3$); MS (APCI): m/z 417 (M+1).

Example 7

2-tert-Butyl-4-methyl-5,6-dimethoxy-8-nitroquinoline

This compound was synthesized using above-mentioned procedure and 4-methyl-5,6-dimethoxy-8-nitroquinoline as the starting material in the presence of trimethylacetic acid.

Yield: 45%; IR (KBr): 1525 and 1340 cm$^{-1}$ ($NO_2$); $^1$H NMR (CDCl$_3$): δ 7.74 (s, 1H, 7-Ar—H), 7.29 (s, 1H, 3-Ar—H), 4.00 (s, 3H, 5-OCH$_3$), 3.96 (s, 3H, 6-OCH$_3$), 2.87 (s, 3H, CH$_3$), 1.38 (s, 9H, 3×CH$_3$), MS (APCI): m/z 305 (M+1).

Example 8

Synthesis of 2-adamantyl-6-methoxy-8-nitroquinoline

6-Methoxy-8-nitroquinoline (1 mmol) (scheme 1) was dissolved in CH$_3$CN (5 mL) while reaction mixture was warmed to 70° C. Silver nitrate (0.6 mmol), 1-adamantanecarboxylic acid (2 mmol), and 10% $H_2SO_4$ (10 mL) was then added to the reaction mixture. A freshly prepared solution of ammonium persulfate (3 mmol) in water (10 mL) was added drop wise to the pre-heated (70° C.) mixture during 10 minutes. The heating source was then removed and reaction proceeded with evolution of carbon dioxide. After 10 minutes, reaction mixture was poured onto ice, and resulting mixture was made alkaline with addition of 30% $NH_4OH$. Extracted with ethyl acetate (4×50 mL), and combined extracts were washed with NaCl solution (2×10 mL). Dried over $Na_2SO_4$ and solvent removed in vacuo to afford oil, which on flash column chromatography over silica gel (230–400 mesh) gave 2-adamantyl-6-methoxy-8-nitroquinoline in good yield.

Yield: 70%; IR (KBr): 1527 cm$^{-1}$ ($NO_2$); $^1$H NMR (CDCl$_3$): δ 8.04 (d, 1H, 4-Ar—H, J=8.7 Hz), 7.61 (d, 1H, 7-Ar—H, J=2.2 Hz), 7.56 (d, 1H, 3-Ar—H, J=8.7 Hz), 7.23 (d, 1H, 5-Ar—H, J=2.4 Hz), 3.95 (s, 3H, OCH$_3$), 2.12 (m, 15H, 12×CH$_2$ and CH); $^{13}$C NMR (CDCl$_3$): δ 168.92, 155.49, 134.58, 128.19, 119.84, 115.31, 109.04, 56.11, 41.57, 39.97, 36.74, 28.67; HRMS (ESI): 339 (M+1).

Synthesis of 5-Cyclopentyl-6-methoxy-8-nitroquinoline and 2,5-dicyclopentyl-6-methoxy-8-nitroquinoline 6-Methoxy-8-nitroquinoline (1 mmol) (scheme 1) was dissolved in CH$_3$CN (5 mL) while reaction mixture was warmed to 70° C. Silver nitrate (0.6 mmol), 1-adamantanecarboxylic acid (2.5 mmol), and 10% $H_2SO_4$ (10 mL) was then added to the reaction mixture. A freshly prepared solution of ammonium persulfate (3 mmol) in water (10 mL) was added drop wise to the pre-heated (70° C.) mixture during 10 minutes. The heating source was then removed and reaction proceeded with evolution of carbon dioxide. After 10 minutes, reaction mixture was poured onto ice, and resulting mixture was made alkaline with addition of 30% $NH_4OH$. Extracted with ethyl acetate (4×50 mL), and combined extracts were washed with NaCl solution (2×10 mL). Dried over $Na_2SO_4$ and solvent removed in vacuo to afford a mixture of mono and dicyclopentyl derivative that was separated by flash column chromatography over silica gel (230–400 mesh) to provide 5-Cyclopentyl-6-methoxy-8-nitroquinoline and 2,5-dicyclopentyl-6-methoxy-8-nitroquinoline.

Example 9

5-Cyclopentyl-6-methoxy-8-nitroquinoline

Yield: 52%; IR (KBr): 1535 and 1215 cm$^{-1}$ ($NO_2$); $^1$H NMR ($CDCl_3$): δ 8.82 (d, 1H, 2-Ar—H, J=4.1 Hz), 8.06 (d, 1H, 4-Ar—H, J=8.3 Hz), 7.42 (m, 1H, 3-Ar—H), 7.14 (s, 1H, 7-Ar—H), 3.98 (s, 3H, $OCH_3$), 3.15 (m, 1H, CH), 1.64 (m. 8H, 4×$CH_2$) MS (EI): m/z 272 (M$^+$).

Example 10

2,5-Dicyclopentyl-6-methoxy-8-nitroquinoline

Yield: 10%; IR (KBr): 1545, 1388 cm$^{-1}$ ($NO_2$); $^1$H NMR ($CDCl_3$): δ 8.09 (d, 1H, 4-Ar—H, J=8 Hz), 7.47 (d, 1H, 3-Ar—H, J=8 Hz), 7.17 (s, 1H, 7-Ar—H), 3.98 (s, 3H, $OCH_3$), 2.82 (m, 2H, 2×CH), 1.74 (m, 16H, 8×$CH_2$); MS (EI): m/z 340 (M$^+$).

Examples listed below are prepared using the protocol described above, and by reacting 6-methoxy-8-nitroquinolines with isobutyric acid and cyclohexanecarboxylic acid respectively.

Example 11

5-Isopropyl-6-methoxy-8-nitroquinoline

Yield: 47%; IR (KBr): 1540 and 1388 cm$^{-1}$ ($NO_2$); $^1$H NMR ($CDCl_3$): δ 8.79 (d, 1H, 2-Ar—H, J=4.1 Hz), 8.07 (d, 1H, 4-Ar—H, J=8.2 Hz), 7.4 (dd, 1H, 3-Ar—H, J=8.2 Hz), 7.14 (s, 1H, 7-Ar—H), 3.95 (s, 3H, $OCH_3$), 3.19 (m, 1H, CH), 1.43 (d, 6H, 2×$CH_3$); $^{13}$C NMR ($CDCl_3$): δ 156.97, 149.81, 134.32, 132.13, 128.01, 122.74, 118.86, 106.61, 56.27, 30.19, 20.69; MS (EI): m/z 246 (M$^+$).

Example 12

2,5-Diisopropyl-6-methoxy-8-nitroquinoline

Yield: 12%; IR (KBr): 1545 and 1395 cm$^{-1}$ ($NO_2$); $^1$H NMR ($CDCl_3$): δ 8.09 (d, 1H, 4-Ar—H, J=8.4 Hz), 7.47 (d, 1H, 3-Ar—H, J=8 Hz), 7.19 (s, 1H, 7-Ar—H), 3.99 (s, 3H, $OCH_3$), 3.22 (m, 1H, 2×CH), 1.52 (d, 6H, 2×$CH_3$), 1.48 (d, 6H, 2×$CH_3$); MS (EI): m/z 288 (M$^+$).

Example 13

5-Cyclohexyl-6-methoxy-8-nitroquinoline

Yield: 43%; IR (KBr): 1533 and 1386 cm$^{-1}$ ($NO_2$); $^1$H NMR ($CDCl_3$): δ 8.79 (d, 1H, 2-Ar—H, J=4 Hz), 8.05 (d, 1H, 4-Ar—H, J=8.3 Hz), 7.43 (dd, 1H, 3-Ar—H, J=8.2 Hz), 7.13 (s, 1H, 7-Ar—H), 3.99 (s, 3H, $OCH_3$), 2.82 (m, 1H, CH), 1.67 (m, 10H, 5×$CH_2$); $^{13}$C NMR ($CDCl_3$): δ 156.37, 128.76, 127.54, 122.29, 106.23, 71.72, 55.87, 40.69, 29.63, 27.65, 26.71, 25.73, 19.09; MS (EI): m/z 286 (M$^+$).

Example 14

2,5-Dicyclohexyl-6-methoxy-8-nitroquinoline

Yield: 11%; IR (KBr): 1537 and 1382 cm$^{-1}$ ($NO_2$); $^1$H NMR ($CDCl_3$): δ 8.09 (d, 1H, 4-Ar—H, J=8.2 Hz), 7.49 (d, 1H, 3-Ar—H, J=8.2 Hz), 7.12 (s, 1H, 7-Ar—H), 3.94 (s, 3H, $OCH_3$), 2.87 (m, 1H, 2×CH), 1.77 (m, 20H, 10×$CH_2$); MS (EI): m/z 368 (M$^+$).

General Procedure for the Synthesis of Ring-Substituted 8-Quinolinamines

A solution of ring-substituted 8-nitroquinoline (5 mmol) in ~95% ethanol (20 mL) was hydrogenated over raney nickel ($T_1$ grade) for ~6 h at 45 psi in a Parr hydrogenator. Catalyst was removed by filtration, and solvent was removed under reduced pressure to provide of ring-substituted 8-quinolinamines as oil, which were subjected to nest step reaction without any further purification.

Example 15

2-tert-Butyl-6-methoxy-8-quinolinamine

Yield: 86%; IR (KBr): 3480 and 3375 cm$^{-1}$ ($NH_2$); $^1$H NMR ($CDCl_3$): δ 7.84 (d, 1H, 4-Ar—H; J=8.6 Hz), 7.41 (d, 1H, 3-Ar—H, J=8.6 Hz), 6.54 (d, 1H, 7-Ar—H, J=2.5 Hz), 6.43 (d, 1H, 5-Ar—H, J=2.5 Hz), 4.98 (bs, 1H, $NH_2$), 3.83 (s, 3H, $OCH_3$), 1.42 (s, 9H, 3×$CH_3$); HRMS (ESI): m/z 231 (M+1).

Example 16

2-Adamantyl-6-methoxy-8-quinolinamine

Yield: 94%; IR (KBr): 3445–3353 cm$^{-1}$ ($NH_2$); $^1$H NMR ($CDCl_3$): δ 7.89 (d, 1H, 4-Ar—H, J=8.6 Hz), 7.41 (d, 1H, 3-Ar—H, J=8.6 Hz), 6.55 (d, 1H, 7-Ar—H, J=2.2 Hz), 6.45 (s, 1H, 5-Ar—H, J=2.1 Hz), 5.21 (bs, 2H, $NH_2$), 3.75 (s, 1H, $OCH_3$) 2.29–1.75 (m, 15H, 12×$CH_2$ and CH); $^{13}$C NMR ($CDCl_3$): δ 163.30, 158.85, 145.86, 134.90, 130.89, 128.82, 118.38, 96.27, 91.65, 55.19, 42.10, 39.30, 37.81, 36.94, 31.94, 29.71, 28.89, 22.71, 14.64, 14.16; HRMS (APCI): m/z 309 (M+1).

Example 17

5-Cyclopentyl-6-methoxy-8-quinolinamine

Yield: 92%; IR (KBr): 2958 and 2928 cm$^{-1}$ ($NH_2$); $^1$H NMR ($CDCl_3$): δ 8.58 (d, 1H, 2-Ar—H), 7.90 (d, 1H, 4-Ar—H), 7.26 (s, 1H, 3-Ar—H), 6.51 (s, 1H, 7-Ar—H), 5.09 (bs, 2H, $NH_2$), 3.89 (s, 3H, $OCH_3$), 3.57 (m, 1H, CH) 1.88 (m, 8H, 4×$CH_2$); MS (EI): m/z 242 (M$^+$).

Example 18

5-Isopropyl-6-methoxy-8-quinolinamine

Yield: 95%; IR (KBr): 3330 cm$^{-1}$ ($NH_2$); $^1$H NMR ($CDCl_3$): δ 7.71 (d, 1H, 2-Ar—H), 7.54 (d, 1H, 4-Ar—H), 6.76 (1H, d, 3-Ar—H), 6.53 (s, 1H, 7-Ar—H), 5.13 (bs, 2H, $NH_2$), 4.22 (s, 3H, $OCH_3$), 3.07 (m, 1H, CH), 1.39 (d, 6H, 2×$CH_3$); MS (EI): m/z 216 (M$^+$).

Example 19

5-Cyclohexyl-6-methoxy-8-quinolinamine

Yield: 82%; IR (KBr): 3008 and 2926 cm$^{-1}$ ($NH_2$); $^1$H NMR ($CDCl_3$): δ 8.59 (d, 1H, 2-Ar—H, J=4 Hz), 7.92 (d, 1H, 4-Ar—H, J=8.4 Hz), 7.26 (d, 1H, 3-Ar—H, J=8.2 Hz), 6.50 (s, 1H, 7-Ar—H), 5.1 (bs, 2H, NH$_2$), 3.89 (s, 3H, OCH$_3$) 3.10 (m, 1H, CH), 1.69 (m, 10H, 5×CH$_2$); MS (EI): m/z 256 (M$^+$).

Example 20

2,5-Dicyclopentyl-6-methoxy-8-quinolinamine

Yield: 90%; IR (KBr): 2930 cm$^{-1}$ (NH$_2$); $^1$H NMR (CDCl$_3$): δ 7.92 (d, 1H, 4-Ar—H), 7.23 (s, 1H, 3-Ar—H), 6.57 (s, 1H, 7-Ar—H), 5.09 (bs, 2H, NH$_2$), 3.89 (s, 3H, OCH$_3$), 3.29 (m, 1H, 2×CH) 1.94 (m, 16H, 8×CH$_2$); MS (EI): m/z 310 (M$^+$).

Example 21

2,5-Diisopropyl-6-methoxy-8-quinolinamine

Yield: 88%; IR (KBr): 3333 cm$^{-1}$ (NH$_2$); $^1$H NMR (CDCl$_3$): δ 7.67 (d, 1H, 4-Ar—H), 6.90 (1H, d, 3-Ar—H), 6.77 (s, 1H, 7-Ar—H), 5.17 (bs, 2H, NH$_2$), 4.15 (s, 3H, OCH$_3$), 3.17 (m, 2H, 2×CH), 1.42 (d, 6H, 2×CH$_3$), 1.37 (d, 6H, 2×CH$_3$); MS (EI): m/z 258 (M$^+$).

Example 22

2,5-Dicyclohexyl-6-methoxy-8-quinolinamine

Yield: 88%; IR (KBr): 3030 cm$^{-1}$ (NH$_2$); $^1$H NMR (CDCl$_3$): δ 7.95 (d, 1H, 4-Ar—H), 7.28 (d, 1H, 3-Ar—H), 6.58 (s, 1H, 7-Ar—H), 5.14 (bs, 2H, NH$_2$), 3.84 (s, 3H, OCH$_3$) 3.23 (m, 2H, 2×CH), 1.77 (m, 20H, 10×CH$_2$); MS (EI): m/z 338 (M$^+$).

Example 23

2-tert-Butyl-5,6-dimethoxy-8-quinolinamine

Yield: 100%; IR (KBr): 3461 cm$^{-1}$ (NH$_2$); $^1$H NMR (CDCl$_3$): δ 8.32 (d, 1H, 4-Ar—H, J=9 Hz), 7.52 (d, 1H, 3-Ar—H, J=9 Hz), 6.81 (s, 1H, 7-Ar—H), 5.1 (bs, 2H, NH$_2$), 3.95 (s, 3H, 5-OCH$_3$), 3.88 (s, 3H, 6-OCH$_3$) 1.51 (s, 9H, 3×CH$_3$); HRMS (ESI): 261.2 (M+1).

Example 24

2-Cyclohexyl-5,6-dimethoxy-8-quinolinamine

Yield: 80%; IR (KBr): 3230 cm$^{-1}$ (NH$_2$); $^1$H NMR (CDCl$_3$): δ 8.33 (d, 1H, 4-Ar—H, J=9.4 Hz), 7.51 (d, 1H, 7-Ar—H, J=9.5 Hz), 6.81 (s, 1H, 7-Ar—H), 5.17 (bs, 2H, NH$_2$, exchangeable with D$_2$O), 3.95 (s, 3H, 5-OCH$_3$), 3.88 (s, 3H, 6-OCH$_3$), 3.1 (m, 1H, CH), 1.45 (m, 10H, 5×CH$_2$); MS (EI): m/z 286 (M$^+$).

Example 25

2-Isopropyl-5,6-dimethoxy-8-quinolinamine

Yield: 100%; IR (KBr): 3355 cm$^{-1}$ (NH$_2$); $^1$H NMR (CDCl$_3$): δ 7.70 (d, 1H, 4-Ar—H), 7.23 (d, 1H, 3-Ar—H), 6.82 (s, 1H, 7-Ar—H), 5.71 (bs, 2H, NH$_2$), 4.14 (s, 3H, 5-OCH$_3$), 4.12 (s, 3H, 6-OCH$_3$), 3.1 (m, 1H, CH), 1.2 (s, 6H, 2×CH$_3$); MS (EI): m/z 246 (M$^+$).

Example 26

2-tert-Butyl-4-ethyl-5-pentoxy-6-methoxy-8-quinolinamine

Yield: 95%; IR (KBr): 3350 cm$^{-1}$ (NH$_2$); $^1$H NMR (CDCl$_3$): δ 7.28 (s, 1H, 3-Ar—H), 6.92 (s, 1H, 7-Ar—H), 4.06 (t, 2H, OCH$_2$), 3.93 (s, 3H, OCH$_3$), 3.27 (q, 2H, CH$_2$), 1.85 (m, 4H, 2×CH$_2$), 1.39 (m, 2H, CH$_2$), 1.40 (s, 3H, 3×CH$_3$), 0.94 (t, 3H, CH$_3$); MS (APCI): m/z 345 (M+1).

Example 27

2-tert-Butyl-4-ethyl-5-octoxy-6-methoxy-8-quinolinamine

Yield: 93%; %; IR (KBr): 3355 cm$^{-1}$ (NH$_2$); $^1$H NMR (CDCl$_3$): δ 7.33 (s, 1H, 3-Ar—H), 6.97 (s, 1H, 7-Ar—H), 4.1 (t, 2H, OCH$_2$), 3.97 (s, 3H, OCH$_3$), 3.29 (q, 2H, CH$_2$), 1.67 (m, 2H, CH$_2$), 1.57 (m, 6H, 3×CH$_2$), 1.41 (s, 9H, 3×CH$_3$), 0.98 (t, 3H, CH$_3$); MS (APCI): m/z 375 (M+1).

Example 28

2-tert-Butyl-4-methyl-5,6-dimethoxy-8-quinolinamine

Yield: 90%; IR (KBr): 3358 cm$^{-1}$ (NH$_2$); $^1$H NMR (CDCl$_3$): δ 7.39 (s, 1H, 3-Ar—H), 6.99 (s, 1H, 7-Ar—H), 4.00 (s, 3H, 5-OCH$_3$), 3.96 (s, 3H, 6-OCH$_3$), 2.89 (s, 3H, CH$_3$), 1.42 (s, 9H, 3×CH$_3$), MS (APCI): m/z 275 (M+1).

Typical Procedure for the Synthesis of Ring-Substituted 2-[4-(6-Methoxy-8-quinolinamino)pentyl]-1,3-isoindolinediones A mixture of ring-substituted 8-quinolinamine (6 mmol), 2-(4-bromopentyl)-1,3-isoindolinedione (6.0 mmol) and triethylamine (6 mmol) was heated at 120° C. with stirring for 3 h. An additional quantity of 2-(4-bromopentyl)-1,3-isoindolinedione (6 mmol) and triethylamine (6 mmol) was added and stirring was continued with heating for 4 h. A third equivalent of 2-(4-bromopentyl)-1,3-isoindolinedione (6 mmol) and triethylamine (6 mmol) was added, and the reaction mixture was heated at 120° C. for 16 h. The reaction mixture was then diluted with ethyl acetate (100 mL) and filtered. The filtrate was basified with 2N NaOH solution and extracted with ethyl acetate (3×50 mL). The combined extracts were washed with water (2×10 mL), dried over Na$_2$SO$_4$ and concentrated under reduced pressure to yield a dark residue that was purified by flash column chromatography on silica gel (230–400 mesh) using ethyl acetate/hexane as eluant to provide ring-substituted 2-[4-(6-methoxy-8-quinolinamino)pentyl]-1,3-isoindoline-diones as oil.

Example 29

2-[4-(2-tert-Butyl-6-methoxy-8-quinolinamino)pentyl]-1,3-isoindolinedione

Yield: 83%; IR (KBr): 3387 cm$^{-1}$ (NH$_2$), 1713 (C=O); $^1$H NMR (CDCl$_3$): δ 7.83 (d, 1H, 4-Ar—H; J=8.5 Hz), 7.80 (m, 4H, Ar—H), 7.41 (d, 1H, 3-Ar—H, J=8.5 Hz), 6.27 (d, 1H, 7-Ar—H, J=2.43 Hz), 6.24 (d, 1H, 5-Ar—H, J=2.4 Hz), 6.13 (bs, 1H, NH), 3.75 (t, 2H, N—CH$_2$), 3.62 (bs, 1H, N—CH), 1.86–1.61 (m, 4H, 2×CH$_2$), 1.41 (s, 9H, 3×CH$_3$), 1.29 (d, 3H, CH$_3$); $^{13}$C NMR (CDCl$_3$): δ 168.39, 163.33, 158.81, 144.71, 134.97, 133.98, 133.50, 132.11, 132.07, 127.27, 123.16, 118.77, 96.75, 91.64, 55.18, 50.53, 47.99, 38.07, 37.97, 37.68, 37.17, 33.98, 30.25, 27.02, 26.46, 25.31, 20.59; MS (EI): m/z 445 (M$^+$).

Example 30

2-[4-(5-Cyclopentyl-6-methoxy-8-quinylamino)pentyl]-1,3-isoindolinedione

Yield: 44%; IR (KBr): 1712 cm$^{-1}$ (C=O); $^1$H NMR (CDCl$_3$): δ 8.56 (d, 1H, 2-Ar—H, J=2.8 Hz), 7.81 (m, 4H, Ar—H), 7.91 (d, 1H, 4-Ar—H, J=7.8 Hz), 7.21 (m, 1H, 3-Ar—H), 6.65 (s, 1H, 7-Ar—H), 5.12 (bs, 1H, NH), 3.89 (s, 3H, OCH$_3$), 3.69 (m, 3H, N—CH and N—CH$_2$) 3.46 (m, 1H, CH), 2.02 (m, 4H, 2×CH$_2$), 1.69 (m, 8H, 4×CH$_2$), 1.22 (d, 3H, CH$_3$); MS (EI): m/z 457 (M$^+$).

Example 31

2-[4-(2-Adamantyl-6-methoxy-8-quinolylamino)pentyl]-1,3-isoindolinedione

Yield: 56%; IR (KBr): 3363 cm$^{-1}$ (NH), 1711 cm$^{-1}$ (C=O); $^1$H NMR (CDCl$_3$): δ 7.86 (d, 1H, 4-Ar—H), 7.81 (m, 4H, Ar—H), 7.38 (d, 1H, 3-Ar—H, J=8.4 Hz), 6.27 (d, 1H, 7-Ar—H), 6.25 (d, 1H, 5-Ar—H), 3.85 (s, 3H, OCH$_3$), 3.69 (m, 3H, N—CH and N—CH$_2$) 1.91 (m, 15H, 12×CH$_2$ and CH), 1.6 (m, 4H, 2×CH$_2$), 1.31 (d, 3H, CH$_3$); $^{13}$C NMR (CDCl$_3$): δ 168.39, 163.18, 158.78, 144.97, 134.85, 133.91, 127.58, 123.16, 118.39, 96.51, 91.54, 69.48, 55.17, 47.89, 42.05, 39.29, 38.79, 38.01, 37.82, 36.94, 34.001, 33.17, 28.88, 27.98, 25. 31, 24.60, 20.66, 19.93; HRMS (APCI): 524 (M+1).

Example 32

2-[4-(5-Isopropyl-6-methoxy-8-quinolylamino)pentyl]-1,3-isoindolinedione

Yield: 53%; IR (KBr): 3433 cm$^{-1}$ (NH), 1709 cm$^{-1}$ (C=O); $^1$H NMR (CDCl$_3$): δ 8.57 (d, 1H, 2-Ar—H, J=3.0 Hz), 8.10 (d, 1H, 4-Ar—H, J=7.9 Hz), 7.83 (m; 4H, Ar—H), 7.37 (dd, 1H, 3-Ar—H, J=8.0 Hz), 6.84 (s, 1H, 7-Ar—H), 4.81 (bs, 1H, NH), 3.86 (s, 3H, OCH$_3$) 3.52 (m, 3H, N—CH and N—CH$_2$), 1.70 (m, 2H, CH$_2$), 1.46 (m, 2H, CH$_2$), 1.32 (d, 6H, 2×CH$_3$), 0.98 (d, 3H, CH$_3$); $^{13}$C NMR (CDCl$_3$): 167.76, 158.49, 145.49, 143.41, 138.41, 138.43, 134.47, 134.21, 131.26, 127.27, 127.05, 122.87, 121.08, 98.27, 54.41, 37.06, 34.06, 34.51, 27.86, 23.90, 20.55; MS (EI): m/z431(M$^+$).

Example 33

2-[4-(5-Cyclohexyl-6-methoxy-8-quinylamino)pentyl]-1,3-isoindolinedione

Yield: 63%; IR (KBr): 3387 cm$^{-1}$ (NH), 1713 cm$^{-1}$ (C=O); $^1$H NMR (CDCl$_3$): δ 8.57 (d, 1H, 2-Ar—H), 7.84 (m, 4H, Ar—H), 7.81 (d, 1H, 4-Ar—H, J=6 Hz), 7.26 (d, 1H, 3-Ar—H, 6.64 (s, 1H, 7-Ar—H), 3.89 (s, 3H, OCH$_3$), 3.68 (t, 2H, N—CH$_2$) 3.32 (m, 1H, N—CH), 3.18 (m, 1H, CH), 2.22 (m, 4H, 2×CH$_2$), 1.5 (m, 10H, 5×CH$_2$), 1.1 (d, 3H, CH$_3$); MS (EI): m/z 501 (M$^+$).

Example 34

2-[4-(2,5-Diyclopentyl-6-methoxy-8-quinylamino)pentyl]-1,3-isoindolinedione

Yield: 89%; IR (KBr): 1715 cm$^{-1}$ (C=O); $^1$H NMR (CDCl$_3$): δ 7.95 (d, 1H, 4-Ar—H, J=7.9 Hz), 7.85 (m, 4H, Ar—H), 7.27 (d, 1H, 3-Ar—H), 6.69 (s, 1H, 7-Ar—H), 5.12 (bs, 1H, NH), 3.89 (s, 3H, OCH$_3$), 3.65 (m, 3H, N—CH and N—CH$_2$) 3.44 (m, 2H, 2×CH), 2.07 (m, 4H, 2×CH$_2$), 1.62 (m, 16H, 8×CH$_2$), 1.21 (d, 3H, CH$_3$); MS (EI): m/z 525 (M$^+$).

Example 35

2-[4-(2,5-Diisopropyl-6-methoxy-8-quinolylamino)pentyl]-1,3-isoindolinedione

Yield: 77%; IR (KBr): 3400 cm$^{-1}$ (NH), 1715 cm$^{-1}$ (C=O); $^1$H NMR (CDCl$_3$): δ 8.12 (d, 1H, 4-Ar—H), 7.80 (m, 4H, Ar—H), 7.35 (d, 1H, 3-Ar—H), 6.87 (s, 1H, 7-Ar—H), 4.82 (bs, 1H, NH), 3.87 (s, 3H, OCH$_3$) 3.53 (m, 3H, N—CH and N—CH$_2$), 3.10 (m, 2H, 2×CH), 1.73 (m, 2H, CH$_2$), 1.49 (m, 2H, CH$_2$), 1.39 (d, 6H, 2×CH$_3$), 1.32 (d, 6H, 2×CH$_3$), 0.98 (d, 3H, CH$_3$); MS (EI): m/z 473 (M$^+$).

Example 36

2-[4-(2,5-Dicyclohexyl-6-methoxy-8-quinylamino)pentyl]-1,3-isoindolinedione

Yield: 88%; IR (KBr): 3360 cm$^{-1}$ (NH), 1713 cm$^{-1}$ (C=O); $^1$H NMR (CDCl$_3$): δ 7.88 (d, 1H, 4-Ar—H), 7.23 (d, 1H, 3-Ar—H), 6.67 (s, 1H, 7-Ar—H), 3.88 (s, 3H, OCH$_3$), 3.65 (t, 2H, N—CH$_2$) 3.33 (m, 1H, N—CH), 3.15 (m, 2H, 2×CH), 2.22 (m, 4H, 2×CH$_2$), 1.65 (m, 20H, 10×CH$_2$), 1.17 (d, 3H, CH$_3$); MS (EI): m/z 553 (M$^+$).

Example 37

2-[4-(2-tert-Butyl-5,6-dimethoxy-8-quinolylamino)pentyl]-1,3-isoindolinedione

Yield: 56.4%; IR (KBr): 3382 cm$^{-1}$ (NH), 1712 cm$^{-1}$ (C=O); $^1$H NMR (CDCl$_3$): δ 8.20 (d, 1H, 4-Ar—H, J=9 Hz), 7.82 (m, 4H, Ar—H), 7.46 (d, 1H, 3-Ar—H, J=9 Hz), 6.38 (s, 1H, 7-Ar—H), 6.02 (bs, 1H, NH), 3.96 (s, 3H, 5-OCH$_3$), 3.84 (s, 3H, 6-OCH$_3$) 3.69 (t, 2H, N—CH$_2$), 3.64 (m, 1H, N—CH), 1.73 (m, 4H, 2×CH$_2$) 1.41 (s, 9H, 3×CH$_3$), 1.31 (d, 3H, CH$_3$); HR MS (ESI): 476.2 (M+1).

Example 38

2-[4-(2-Cyclohexyl-5,6-dimethoxy-8-quinylamino)pentyl]-1,3-isoindolinedione

Yield: 70%; IR (KBr): 3350 cm$^{-1}$ (NH$_2$), 1720 cm$^{-1}$ (C=O); $^1$H NMR (CDCl$_3$): δ 8.22 (d, 1H, 4-Ar—H, J=9.2 Hz), 7.75 (m, 4H, Ar—H), 7.46 (d, 1H, 3-Ar—H, J=9.2 Hz), 6.39 (s, 1H, 7-Ar—H), 6.0 (bs, 1H, NH), 3.96 (s, 3H, 5-OCH$_3$), 3.84 (s, 3H, 6-OCH$_3$) 3.69 (t, 2H, N—CH$_2$), 3.64 (m, 1H, CH), 1.75 (m, 4H, 2×CH$_2$) 1.41 (m, 10H, 5×CH$_2$), 1.35 (d, 3H, CH$_3$); MS (EI): m/z 501 (M$^+$) 469.

Example 39

2-[4-(2-Isopropyl-5,6-dimethoxy-8-quinolylamino)pentyl]-1,3-isoindolinedione

Yield: 49%; IR (KBr): 3260 cm$^{-1}$ (NH$_2$), 1720 cm$^{-1}$ (C=O); $^1$H NMR (CDCl$_3$): δ 8.10 (d, 1H, 4-Ar—H, J=7.9 Hz), 7.82 (m, 4H, Ar—H), 7.40 (m, 5H, Ar—H), 7.37 (dd, 1H, 3-Ar—H, J=8.0 Hz), 6.84 (s, 1H, 7-Ar—H), 4.81 (bs, 1H, NH), 3.97 (s, 3H, 5-OCH$_3$), 3.86 (s, 3H, 6-OCH$_3$) 3.52 (m, 3H, N—CH and N—CH$_2$), 1.70 (m, 2H, CH$_2$), 1.46 (m, 2H, CH$_2$), 1.32 (d, 6H, 2×CH$_3$), 0.98 (d, 3H, CH$_3$); MS (EI): m/z 462 (M$^+$).

Example 40

2-[4-(2-tert-Butyl-4-ethyl-6-methoxy-5-pentoxy-quinolin-8-ylamino)-pentyl]-isoindole-1,3-dione Yield: 67%; yellow oil; IR (KBr): 3379 cm$^{-1}$ (NH$_2$), 1712 (C=O); $^1$H NMR (CDCl$_3$): 7.82 (m, 2H, Ar—H), 7.71 (m, 2H, Ar—H), 7.10 (d, 1H, 3-Ar—H, J=4.4 Hz), 6.44 (s, 1H, 7-Ar—H), 6.07 (bs, 1H, NH), 3.96 (s, 3H, OCH$_3$), 3.87 (t, 2H, OCH$_2$, J=6.9 Hz), 3.75–3.67 (m, 3H, N—CH, and N—CH$_2$), 3.24 (m, 2H, CH$_2$), 1.85–1.41 (m, 10H, 5×CH$_2$), 1.34 (s, 9H, 3×CH$_3$), 1.3 (m, 6H, 2×CH$_3$), 0.95 (t, 3H, CH$_3$, J=7.9 Hz); HRMS (APCI): m/z 560 (M+1).

Example 41

2-[4-(2-tert-Butyl-4-ethyl-6-methoxy-5-octoxy-quinolin-8-ylamino)-pentyl]-isoindole-1,3-dione Yield: 75%; yellow oil; IR (KBr): 3407 cm$^{-1}$ (NH$_2$), 1713 (C=O); $^1$H NMR (CDCl$_3$): 7.82 (m, 2H, Ar—H), 7.71 (m, 2H, Ar—H), 7.10 (d, 1H, 3-Ar—H, J=4.4 Hz), 6.44 (s, 1H, 7-Ar—H), 6.07 (bs, 1H, NH), 3.96 (s, 3H, OCH$_3$), 3.87 (t, 2H, OCH$_2$, J=6.9 Hz), 3.75–3.67 (m, 3H, N—CH, and N—CH$_2$), 3.25 (m, 2H, CH$_2$), 1.89–1.61 (m, 16H, 8×CH$_2$), 1.37 (m, 9H, 3×CH$_3$), 1.30 (m, 6H, 2×CH$_3$), 1.04 (t, 3H, CH$_3$, J=7.9 Hz); HRMS (APCI): m/z 602 (M+1).

Example 42

2-[4-(2-tert-Butyl-5,6-methoxy-4-methyl-quinolin-8-ylamino)-pentyl]-isoindole-1,3-dione Yield: 87%; yellow oil; IR (KBr): 3410 cm$^{-1}$(NH$_2$), 1713 (C=O); $^1$H NMR (CDCl$_3$): 7.85 (m, 2H, Ar—H), 7.75 (m, 2H, Ar—H), 7.13 (d, 1H, 3-Ar—H, J=4.4 Hz), 6.49 (s, 1H, 7-Ar—H), 6.03 (bs, 1H, NH), 4.01 (s, 3H, OCH$_3$), 3.96 (s, 3H, OCH$_3$), 3.63 (m, 3H, N—CH, and N—CH$_2$), 2.59 (t, 2H, CH$_2$), 1.60 (m 4H, 2×CH$_2$), 1.34 (s, 9H, 3×CH$_3$), 1.23 (m, 3H, CH$_3$); HRMS (APCI): m/z 504 (M+1).

Typical Procedure for the Synthesis of Ring-Substituted N$^8$-(4-Amino-1-methylbutyl)-6-methoxy-8-quinolinamine To a solution of ring-substituted 2-[4-(6-methoxy-8-quinolinamino)pentyl]-1,3-isoindolinedione (4 mmol) in 95% ethanol (20 mL), was added hydrazine hydrate (100 mmol) and the reaction mixture was stirred with refluxing for 6 h. Solvent was removed under reduced pressure and the residue was diluted with water (20 mL). The reaction mixture was basified with 8N NaOH solution, extracted with chloroform (3×20 mL), washed with water, dried over sodium sulfate and concentrated under reduced pressure to yield ring-substituted N$^8$-(4-amino-1-methylbutyl)-6-methoxy-8-quinolinamine (14) as oil, which on treatment with ethereal Hydrochloric acid provided ring-substituted N$^8$-(4-amino-1-methylbutyl)-6-methoxy-8-quinolinamine dihydrochloride.

Example 43

N$^8$-(4-Amino-1-methylbutyl)-2-tert-butyl-6-methoxy-8-quinolinamine

Yield: 90%; IR (KBr): 3393 cm$^{-1}$ (NH), 3019–2968 cm$^{-1}$ (amine); $^1$H NMR (free base, CDCl$_3$): δ 7.84 (d, 1H, 4-Ar—H, J=8.6 Hz), 7.42 (d, 1H, 3-Ar—H, J=8.5 Hz), 6.30 (dd, 1H, 7-Ar—H, J=2.3 Hz), 6.25 (dd, 1H, 5-Ar—H, J=2.2 Hz), 6.16 (bs, 1H, NH), 3.87 (s, 3H, OCH$_3$), 3.61(bs, 1H, N—H), 2.73 (t, 2H, N—CH$_2$), 1.59 (m, 4H, 2×CH$_2$), 1.42 (s, 9H, 3×CH$_3$), 1.31 (d, 3H, CH$_3$); $^{13}$C NMR (CDCl$_3$): δ 163.36, 158.83, 144.86, 134.96, 133.56, 127.48, 118.80, 96.71, 91.60, 55.19, 47.93, 41.22, 40.59, 37.70, 33.95, 30.28, 29.69, 27.67, 26.66, 20.72, 20.63; HRMS (ESI): m/z 316 (M+1).

Example 44

N$^8$-(4-Amino-1-methylbutyl)-5-cyclopentyl-6-methoxy-8-quinolinamine

Yield: 62%; IR (KBr): 3294 cm$^{-1}$ (NH); 2953–2864 cm$^{-1}$ (amine); $^1$H NMR (free base, CDCl$_3$): δ 8.59 (d, 1H, 2-Ar—H), 7.94 (d, 1H, 4-Ar—H), 7.26 (m, 1H, 3-Ar—H), 6.67 (s, 1H, 7-Ar—H), 3.89 (s, 3H, OCH$_3$), 3.71 (m, 1H, N—CH) 3.48 (m, 2H, N—CH$_2$) 3.12 (m, 1H, CH), 2.64 (m, 4H, 2×CH$_2$) 1.75 (m, 8H, 4×CH$_2$), 1.11 (d, 1H, CH$_3$); MS (EI): m/z 327 (M$^+$).

Example 45

N$^8$-[4-Amino-1-methylbutyl)-2-adamantyl-6-methoxy-8-quinolinamine

Yield: 88%; IR (KBr): 3384 cm$^{-1}$ (amine); $^1$H NMR (free base, CDCl$_3$): δ 7.86 (d, 1H, 4-Ar—H, J=8.6 Hz), 7.39 (d, 1H, 3-Ar—H, J=8.6 Hz), 6.29 (d, 1H, 7-Ar—H), 6.26 (d, 1H, 5-Ar—H), 6.17 (bs, 1H, NH), 3.87 (s, 3H, OCH$_3$), 3.59 (m, 1H, N—CH), 2.75 (m, 2H, N—CH$_2$), 1.97 (m, 15H, 12×CH$_2$ and CH) 1.32 (d, 3H, CH$_3$); $^{13}$C NMR (CDCl$_3$): δ 163.18, 158.84, 45.10, 134.90, 133.86, 127.63, 118.41, 96.43, 91.38, 69.94, 55.19, 48.10, 42.11, 39.30, 38.86, 36.95, 36.56, 34.19, 33.24, 30.17, 29.71, 28.89, 28.01, 20.69, 19.97; HR MS (ESI): 394 (M+1).

Example 46

N$^8$-(4-Amino-1-methylbutyl)-5-isopropyl-6-methoxy-8-quinolinamine

Yield: 61%; IR (KBr): 3422 cm$^{-1}$ (NH); $^1$H NMR (free base, CDCl$_3$): δ 8.61 (d, 1H, 2-Ar—H), 8.1 (d, 1H, 4-Ar—H), 7.61 (dd, 1H, 3-Ar—H), 7.11 (s, 1H, 7-Ar—H), 3.49 (s, 3H, OCH$_3$), 3.25 (m, 3H, N—CH and N—CH$_2$), 2.71 (m, 1H, CH), 1.52 (d, 6H, 2×CH$_3$), 1.15 (d, 3H, CH$_3$); MS (EI): m/z 301 (M$^+$).

Example 47

N$^8$-(4-Amino-1-methylbutyl)-5-cyclohexyl-6-methoxy-8-quinolinamine

Yield: 59%; IR (KBr): 3417 cm$^{-1}$ (NH); $^1$H NMR (free base, CDCl$_3$): δ 8.47 (d, 1H, 2-Ar—H), 7.97 (d, 1H, 4-Ar—H), 7.24 (d, 1H, 3-Ar—H), 6.68 (s, 1H, 7-Ar—H), 3.91 (s, 3H, OCH$_3$), 3.73 (m, 1H, N—CH) 3.48 (m, 2H, N—CH$_2$) 3.12 (m, 1H, CH), 2.64 (m, 4H, 2×CH$_2$) 1.75 (m, 10H, 5×CH$_2$), 1.11 (d, 1H, CH$_3$); MS (EI): m/z 341 (M$^+$).

Example 48

N$^8$-(4-Amino-1-methylbutyl)-2,5-dicyclopentyl-6-methoxy-8-quinolinamine

Yield: 75%; IR (KBr): 3300 cm$^{-1}$ (NH); 2955 cm$^{-1}$ (amine); $^1$H NMR (free base, CDCl$_3$): δ 7.98 (d, 1H, 4-Ar—H), 7.22 (d, 1H, 3-Ar—H), 6.61 (s, 1H, 7-Ar—H), 3.89 (s, 3H, OCH$_3$), 3.71 (m, 1H, N—CH) 3.45 (m, 2H, N—CH$_2$) 3.15 (m, 2H, 2×CH), 2.65 (m, 4H, 2×CH$_2$) 1.79 (m, 16H, 8×CH$_2$), 1.2 (d, 1H, CH$_3$); MS (EI): m/z 395 (M$^+$).

Example 49

N$^8$-(4-Amino-1-methylbutyl)-2,5-diisopropyl-6-methoxy-8-quinolinamine

Yield: 79%; IR (KBr): 3430 cm$^{-1}$ (NH); $^1$H NMR (free base, CDCl$_3$): δ 8.15 (d, 1H, 4-Ar—H), 7.65 (d, 1H, 3-Ar—H), 7.18 (s, 1H, 7-Ar—H), 3.45 (s, 3H, OCH$_3$), 3.29 (m, 3H, N—CH and N—CH$_2$), 2.73 (m, 2H, 2×CH), 1.55 (d, 6H, 2×CH$_3$), 1.54 (d, 6H, 2×CH$_3$), 1.19 (d, 3H, CH$_3$); MS (EI): m/z 343 (M$^+$).

Example 50

N$^8$-(4-Amino-1-methylbutyl)-2,5-dicyclohexyl-6-methoxy-8-quinolinamine

Yield: 55%; IR (KBr): 3400 cm$^{-1}$ (NH); $^1$H NMR (free base, CDCl$_3$): δ 7.93 (d, 1H, 4-Ar—H), 7.28 (d, 1H, 3-Ar—H), 6.75 (s, 1H, 7-Ar—H), 3.95 (s, 3H, OCH$_3$), 3.71 (m, 1H, N—CH) 3.42 (m, 2H, N—CH$_2$) 3.05 (m, 2H, 2×CH), 2.62 (m, 4H, 2×CH$_2$) 1.78 (m, 20H, 10×CH$_2$), 1.15 (d, 1H, CH$_3$); MS (EI): m/z 423 (M$^+$).

Example 51

N$^8$-(4-Amino-1-methylbutyl)-2-tert-butyl-5,6-dimethoxy-8-quinolinamine

Yield: 96%; IR (KBr): 3388 cm$^{-1}$ (NH), 2958 cm$^{-1}$ (amine); $^1$H NMR (free base, CDCl$_3$): □ 8.23 (d, 1H, 4-Ar—H, J=9 Hz), 7.48 (d, 1H, 3-Ar—H, J=9 Hz), 6.40 (s, 1H, 7-Ar—H), 6.03 (bs, 1H, NH), 3.97 (s, 3H, 5-OCH$_3$), 3.86 (s, 3H, 6-OCH$_3$) 3.62 (m, 1H, N—CH), 2.78 (t, 2H, N—CH$_2$), 1.78 (m, 4H, 2×CH$_2$), 1.42 (s, 9H, 3×CH$_3$), 1.33 (d, 3H, CH$_3$); MS (EI): 345 (M$^+$).

Example 52

N$^8$-(4-Amino-1-methylbutyl)-2-cyclohexyl-5,6-dimethoxy-8-quinolinamine

Yield: 67%; IR (KBr): 3310 cm$^{-1}$ (NH$_2$); $^1$H NMR (free base, CDCl$_3$): δ 8.21 (d, 1H, 4-Ar—H, J=9.2 Hz), 7.49 (d, 1H, 3-Ar—H, J=9 Hz), 6.41 (s, 1H, 7-Ar—H), 6.03 (bs, 1H, NH), 3.97 (s, 3H, 5-OCH$_3$), 3.86 (s, 3H, 6-OCH$_3$) 3.62 (m, 1H, N—CH), 2.78 (t, 2H, N—CH$_2$), 1.78 (m, 4H, 2×CH$_2$), 1.42 (m, 10H, 5×CH$_2$), 1.31 (d, 3H, CH$_3$); MS (EI): m/z 368 (M$^+$).

Example 53

N$^8$-(4-Amino-1-methylbutyl)-2-isopropyl-5,6-dimethoxy-8-quinolinamine

Yield: 95%; IR (KBr): 3330 cm$^{-1}$ (NH), 2900 cm$^{-1}$ (NH$_2$); $^1$H NMR (free base, CDCl$_3$): δ 8.18 (d, 1H, 4-Ar—H, J=7.8 Hz), 7.35 (m, 1H, 3-Ar—H), 6.87 (s, 1H, 7-Ar—H), 3.95 (s, 3H, 5-OCH$_3$), 3.82 (s, 3H, 6-OCH$_3$) 3.55 (m, 3H, NCH and N—CH$_2$), 1.70 (m, 2H, CH$_2$), 1.46 (m, 2H, CH$_2$), 1.32 (d, 6H, 2×CH$_3$), 0.98 (d, 3H, CH$_3$); HRMS (ESI): m/z 331 (M+1).

Example 54

N$^8$-(4-Amino-1-methylbutyl)-2-tert-butyl-4-ethyl-6-methoxy-5-pentoxy-8-quinolin-amine Yield: 98%; $^1$H NMR (free base, CDCl$_3$): δ 6.91 (s, 1H, 3-Ar—H), 6.43 (s, 1H, 7-Ar—H), 3.94 (s, 3H, 5-OCH$_2$), 3.73 (s, 3H, OCH$_3$) 2.70 (m, 3H, N—CH and N—CH$_2$), 2.60 (m, 2H, CH$_2$), 1.50 (m, 6H, 3×CH$_2$), 1.34 (s, 9H, 3×CH$_3$), 1.30 (m, 4H, 2×CH$_2$), 1.23 (m, 3H, CH$_3$), 0.96 (m, 3H, CH$_3$); HRMS (ESI): m/z 430 (M+1).

Example 55

N$^8$-(4-Amino-1-methylbutyl)-2-tert-butyl-4-ethyl-6-methoxy-5-octoxy-8-quinolin-amine Yield: 99%; $^1$H NMR (free base, CDCl$_3$): δ 6.95 (s, 1H, 3-Ar—H), 6.49 (s, 1H, 7-Ar—H), 3.97 (s, 3H, 5-OCH$_2$), 3.75 (s, 3H, OCH$_3$) 2.72 (m, 3H, N—CH and N—CH$_2$), 2.61 (m, 2H, CH$_2$), 1.53 (m, 10H, 5×CH$_2$), 1.35 (s, 9H, 3×CH$_3$), 1.31 (m, 6H, 3×CH$_2$), 1.21 (m, 3H, CH$_3$), 0.99 (m, 3H, CH$_3$); HRMS (ESI): m/z 472 (M+1).

Example 56

N$^8$-(4-Amino-3-methylbutyl)-2-tert-butyl-5,6-methoxy-4-methyl-8-quinolinamine

Yield: 89%; $^1$H NMR (free base, CDCl$_3$): δ 6.99 (s, 1H, 3-Ar—H), 6.49 (s, 1H, 7-Ar—H), 3.73 (s, 6H, 2×OCH$_3$) 2.79 (m, 3H, N—CH and N—CH$_2$), 2.37 (s, 3H, CH$_3$), 1.53 (m, 4H, 2×CH$_2$), 1.35 (s, 9H, 3×CH$_3$), 1.23 (m, 3H, CH$_3$); HRMS (ESI): m/z 360 (M+1).

Typical Procedure for the Synthesis of Ring-Substituted Protected Amino Acid Quinoline Derivatives To an ice cooled stirred solution of ring-substituted N$^8$-(4-amino-1-methylbutyl)-6-methoxy-8-quinolinamine [(free base), 1 mol] and suitably N-protected amino acid (1.1 mol) in dichloromethane (15 mL), 1,3-dicyclohexylcarbodiimide (1.1 mol) was added. Reaction mixture was allowed to attain room temperature and stirring was continued for another 4 h. The reaction mixture was kept in refrigerator overnight and the separated 1,3-dicyclohexylurea (DCU) filtered, and filtrate was concentrated under reduced pressure. Ethyl acetate was added to the residue and the additional quantity of separated DCU was again removed by filtration. The filtrate was washed with saturated sodium bicarbonate solution (3×10 mL) followed by water (2×10 mL), and dried over Na$_2$SO$_4$. The solvent was removed in vacuo to afford the crude product, which was purified by flash column chromatography on silica gel (230–400 mesh) using 2% methanol in chloroform to afford the product.

Example 57

{4-Benzyloxycarbonylamino-4-[2-tert-butyl-6-methoxy-quinolin-8-ylamino)-pentyl-carbamoyl]-butyl}-carbamic acid benzyl ester Yield: 98%; IR (KBr): 3430 cm$^{-1}$ (NH), 1714 cm$^{-1}$ (ester), 1666 cm$^{-1}$ (amide carbonyl); $^1$H NMR (CDCl$_3$): δ 7.85 (d, 1H, 4-Ar—H, J=8.6 Hz), 7.42 (d, 1H, 3-Ar—H, J=8.6 Hz) 10H, Ar—H), 6.44 (bs, 1H, NH), 6.29 (s, 3H, 7-Ar—H), 6.24 (s, 1H, 5-Ar—H), 6.12 (bs, 1H, NH), 5.56 (bs, H, NH), 5.50 (bs, 1H, NH), 5.08 (m, 4H, 2×OCH$_2$Ph), 4.36 (bs, 1H, N—CH), 4.23 (bs, 1H, N—CH), 3.88 (s, 3H, OCH$_3$), 3.72 (s, 4H, 2×N—CH$_2$), 3.56 (bs, 1H, N—CH), 3.21 (m, 4H, 2×CH$_2$), 1.55 (m, 4H, 2×CH$_2$), 1.42 (s, 9H, 3×CH$_3$), 1.26 (d, 3H, CH$_3$); $^{13}$C NMR (CDCl$_3$): δ 172.61, 171.59, 163.35, 158.73, 156.95, 156.40, 155.90, 144.80, 136.22, 134.99, 133.53, 128.22, 128.22, 128.12, 118.83, 96.61, 91.48, 55.16, 53.50, 52.50, 47.84, 40.43, 39.66, 37.67, 33.83, 29.91, 29.58, 26.05, 25.89, 20.59, 14.19; HRMS (APCI) m/z 698 (M+1).

Example 58

{1-4-[2-tert-Butyl-6-methoxy-quinolin-8-ylamino)-pentylcarbamoyl]-ethyl}-carbamic acid benzyl ester Yield: 93%; IR (KBr): 3293 cm$^{-1}$ (NH), 1647 (amide carbonyl); $^1$H NMR (CDCl$_3$): δ 7.88 (d, 1H, 4-Ar—H, J=8.5 Hz), 7.44 (d, 1H, 3-Ar—H, J=8.6 Hz), 7.33 (m, 5H, Ar—H), 6.32 (s, 1H, 7-Ar—H), 6.27 (s, 1H, 5-Ar—H), 5.88 (bs, 1H, NH), 5.34 (bs, 1H, NH), 5.08 (s, 2H, OCH$_2$Ph), 3.87 (s, 4H, OCH$_3$ and N—CH), 3.59 (s, 1H, N—CH), 3.30 (s, 2H, N—CH$_2$), 1.66 (m, 4H, 2×CH$_2$), 1.42 (s, 9H, 3×CH$_3$), 1.31 (d, 3H, CH$_3$), 0.91 (m, 6H, 2×CH$_3$); $^{13}$C NMR (CDCl$_3$): δ 171.03, 158.81, 135.09, 128.17, 118.86, 96.90, 91.63, 67.03, 60.63, 55.20, 48.02, 39.49, 37.70, 33.84, 30.26, 26.08, 25.62, 24.94, 20.57, 19.83, 19.26 , 17.71, 14.21; HRMS (ESI) m/z 549 (M+1).

Example 59

{5-Benzyloxycarbonylamino-5-[4-(2-tert-butyl-6-methoxy-quinolin-8-ylamino)-pentyl-carbamoyl]-pentyl}-carbamic acid benzyl ester Yield: 91%; IR (KBr): 3304 cm$^{-1}$ (NH), 1719 cm$^{-1}$ (ester), 1690 cm$^{-1}$ (amide carbonyl); $^1$H NMR (CDCl$_3$): δ

7.86 (d, 1H, 4-Ar—H, J=8.6 Hz), 7.43 (d, 1H, 3-Ar—H, J=8.6 Hz), 7.31 (m, 10H, Ar—H), 6.31 (s, 1H, 7-Ar—H), 6.25 (s, 1H, 5-Ar—H), 6.15 (bs, 1H, NH), 5.50 (bs, 1H, NH), 5.07 (s, 4H, 2×OCH$_2$Ph), 4.82 (bs, 1H, NH), 4.13 (m, 1H, CH), 3.85 (s, 3H, OCH$_3$), 3.58 (s, 1H, N—CH), 3.27 (s, 2H, N—CH$_2$), 3.12 (s, 2H, N—CH$_2$), 1.67 (m, 10H, 5×CH$_2$), 1.41(s, 9H, 3×CH$_3$), 1.25 (d, 3H, CH$_3$); $^{13}$C NMR (CDCl$_3$): δ 171.52, 163.44, 158.7, 156.63, 156.34, 144.76, 136.59 136.18, 135.07, 133.55, 128.07, 127.53, 118.86, 96.76, 91.63, 67.05, 55.19, 53.50, 47.95, 40.23, 39.48, 33.79, 31.88, 30.26, 29.38, 26.07, 22.31, 20.59, 14.20; HRMS (ESI) m/z 712 (M+1).

Example 60

{1-[4-(2-tert-Butyl-6-methoxy-8-ylamino)-pentylcarbamoyl]-2-methyl-propyl}-carbamic acid tert-butyl ester Yield: 100%; IR (KBr): 3394 cm$^{-1}$ (NH), 1712 (ester), 1655 (amide carbonyl); $^1$H NMR (CDCl$_3$): δ 7.87 (d, 1H, 4-Ar—H, J=8.5 Hz), 7.43 (d, 1H, 3-Ar—H, J=8.3 Hz), 6.31 (s, 1H, 7-Ar—H), 6.25 (s, 1H, 5-Ar—H), 6.20 (bs, 1H, NH), 5.04 (bs, 1H, NH), 4.13 (m, 1H, N—CH), 3.87 (s, 3H, OCH$_3$), 3.60 (m, 1H, N—CH), 3.30 (m, 2H, N—CH$_2$) 1.68 (m, 4H, 2×CH$_2$), 1.42 (s, 9H, 3×CH$_3$), 1.39 (s, 9H, 3×CH$_3$), 1.31 (d, 4H, 2×CH$_2$); $^{13}$C NMR (CDCl$_3$): δ 172.55, 163.35, 158.7, 155.55, 144.84, 135.00. 133.58, 127.49, 118.49, 118.80, 96.66, 91.50, 60.41, 54.74, 50.83, 50.18, 49.14, 47.93, 39.44, 37.69, 33.95, 32.66, 31.71, 30.27, 28.30, 29.38, 26.18, 25.62, 25.51, 25.36, 21.05, 20.64, 18.61, 14.20; HRMS (ESI) m/z 487 (M+1).

Typical Procedure for the Synthesis of Ring-Substituted N$^1$-[4-(6-methoxy-8-quinolylamino)pentyl]-(2S)-2-amino/diaminoalkanamides To a mixture of ring-substituted benzyl esters (0.5 mmol), glacial acetic acid (1 mL) and 10% Pd—C (0.1 g) in methanol (20 mL) was bubbled hydrogen gas for 1 h. The catalyst was filtered and filtrate was concentrated in vacuo to afford the product as oily syrup, which on treatment with a solution of ethereal HCl provided the corresponding hydrochloride salt derivatives. Alternatively, in the cases involving the use of t-Boc protected amino acids, a solution of protected derivative (0.5 mmol) in methanolic hydrogen chloride (20 mL) was stirred for overnight at room temperature. The solvent was removed in vacuo to afford orange solid. Recrystallized from methanol/diethyl ether.

Example 61

N$^1$-[4-(2-tert-Butyl-6-methoxy-8-quinolylamino)pentyl]-(2S)-2,5-diaminopentamide Yield: 99%; IR (KBr): 3018 cm$^{-1}$ (NH$_2$); $^1$H NMR (free base, CDCl$_3$): δ 8.92 (bs, 4H, 2×NH$_2$), 7.85 (d, 1H, 4-Ar—H), 7.42 (d, 1H, 3-Ar—H), 6.30 (bs, 1H, 7-Ar—H), 6.23 (s, 1H, 5-Ar—H), 3.85 (s, 3H, OCH$_3$), 3.58 (s, 1H, N—CH), 3.44 (s, 1H, N—CH), 3.25 (s, 4H, 2×N—CH$_2$), 2.95 (m, 4H, 2×CH$_2$), 1.40 (s, 9H, 3×CH$_3$), 1.26 (d, 3H, CH$_3$); $^{13}$C NMR (CDCl$_3$): δ 177.38, 170.11, 163.32, 158.79, 144.85, 134.99, 133.57, 127.47, 118.79, 96.61, 91.46, 55.13, 52.68, 49.67, 47.82, 41.74, 39.78, 39.74, 37.66, 34.11, 33.67, 30.24, 28.90, 25.85, 24.85, 22.98, 22.16, 20.73; HRMS (ESI) m/z 429 (M+1).

Example 62

N$^1$-[4-(2-tert-Butyl-6-methoxy-8-quinolylamino)pentyl]-(2S)-2-amino-3-methyl-butanamide Yield: 94%; IR (KBr): 3243 cm$^{-1}$ (NH$_2$), 1663 cm$^{-1}$ (CONH); $^1$H NMR (free base, CDCl$_3$): δ 7.86 (d, 1H, 4-Ar—H, J=8.5 Hz), 7.61 (bs, 1H, NH), 7.43 (d, 1H, 3-Ar—H, J=8.5 Hz), 6.31 (s, 1H, 7-Ar—H), 6.26 (s, 1H, 5-Ar—H), 3.87 (s, 3H, OCH$_3$), 3.62 (s, 1H, N—CH) 3.35 (m, 2H, N—CH$_2$), 2.72 (s, 1H, N—CH), 1.68 (m, 4H, 2×CH$_2$), 1.41 (s, 9H, 3×CH$_3$), 1.29 (d, 3H, CH$_3$), 0.945 (m, 6H, 2×CH$_3$); $^{13}$C NMR (CDCl$_3$): δ 176.68, 171.63, 163.34, 158.86, 144.89, 134.98, 133.6, 127.49, 118.79, 96.69, 91.50, 67.47, 55.17, 47.90, 43.02, 39.24, 37.69, 34.16, 33.74, 30.80, 30.27, 26.16. 25.56, 24.87, 21.50, 20.65, 19.39, 18.90, 18.23, 16.57, 13.94; HRMS (ESI) m/z 414 (M+1).

Example 63

N$^1$-[4-(2-tert-Butyl-6-methoxy-8-quinolylamino)pentyl]-(2S)-2-6-diaminohexanamide Yield: 100%; IR (KBr): 3435 cm$^{-1}$ (NH$_2$), 1667 cm$^{-1}$ (amide carbonyl); $^1$H NMR (free base, CDCl$_3$): δ 7.85 (d, 1H, 4-Ar—H, J=8.5 Hz), 7.42 (d, 1H, 3-Ar—H, J=8.5 Hz), 6.29 (s, 1H, 7-Ar—H), 6.24 (s, 1H, 5-Ar—H), 5.64 (bs, 4H, 2×NH$_2$), 3.89 (s, 3H, OCH$_3$), 3.68 (s, 1H, N—CH), 3.24 (m, 4H, 2×N—CH$_2$), 2.87 (bs, 1H, N—CH), 1.63 (m, 10H, 2×CH$_2$), 1.41 (s, 9H, 3×CH$_3$), 1.24 (d, 3H, CH); HRMS (ESI) m/z 444 (M+1).

Example 64

N$^1$-[4-(2-tert-Butyl-6-methoxy-8-quinolylamino)pentyl]-(2S)-2-aminopropanamide Yield: 98%; IR (KBr): 3018 cm$^{-1}$ (NH$_2$), 1710 cm$^{-1}$ (amide carbonyl); $^1$H NMR (free base, CDCl$_3$): δ 7.86 (d, 1H, 4-Ar—H), 7.65 (d, 1H, 3-Ar—H), 7.15 (s, 1H, 7-Ar—H), 6.81 (s, 1H, 5-Ar—H), 5.48 (bs, 1H, NH), 4.3 (bs, 1H, NH), 3.99 (m, 1H, N—CH), 3.71 (m, 1H, N—CH), 1.84(m, 4H, 2×CH$_2$), 1.50 (s, 9H, 3×CH$_3$), 1.25 (d, 6H, 2×CH$_3$); HRMS (ESI) m/z 387 (M+1).

Advantages

1. This compound proven to be successful for the treatment of relapsing malaria;
2. The molecule can easily be synthesized and inexpensive to produce
3. 8-aminoquinolines analogous exhibit activity against all the stages including that of blood- and tissue-stages of the human malaria life cycle;
4. The molecule is effective against drug resistant strains of P. falciparum.
5. The most effective molecule is also devoid of methemoblobin toxicity traditionally associated with 8-aminoquinoline class of antimalarial drugs.

What is claimed is:

1. A ring-substituted 8-aminoquinoline analog as of formula 1

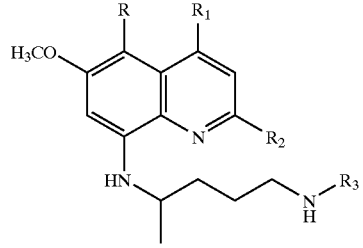

wherein R represents H, straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups; $R_1$ represents H, $CH_3$ and $C_2H_5$; $R_2$ represents straight chain alkyl group containing 1 to 5 carbons, branched alkyl groups, and cycloalkyl group containing 3 to 15 carbon atoms; $R_3$ represents a (R)- or (S)-amino acid, an L-unnatural amino acid, or $R_3$ is H where (a) $R_1$ is H and $R_2$ is selected from the group consisting of $C(CH_3)_3$, 1-adamantyl, c-$C_5H_9$, $CH(CH_3)_2$, c-$C_6H_{11}$, and $C(CH_3)_3$, or (b) where $R_1$ is $CH_3$ or $C_2H_5$ and $R_2$ is $C(CH_3)_3$.

2. A ring substituted 8-aminoquinoline analog as claimed in claim 1, wherein the value of R, R1, R2 and R3 of compound formula 1 are given below:

| R | $R_1$ | $R_2$ | $R_3$ |
|---|---|---|---|
| H | H | $C(CH_3)_3$ | H |
| c-$C_5H_9$ | H | H | H |
| H | H | 1-adamantyl | H |
| $CH(CH_3)_2$ | H | H | H |
| c-$C_6H_{11}$ | H | H | H |
| c-$C_5H_9$ | H | c-$C_5H_9$ | H |
| $CH(CH_3)_2$ | H | $CH(CH_3)_2$ | H |
| c-$C_6H_{11}$ | H | c-$C_6H_{11}$ | H |
| $OCH_3$ | H | $C(CH_3)_3$ | H |
| $OCH_3$ | H | c-$C_6H_{11}$ | H |
| $OCH_3$ | H | $CH(CH_3)_2$ | H |
| $OC_5H_{11}$ | $C_2H_5$ | $C(CH_3)_3$ | H |
| $OC_8H_{17}$ | $C_2H_5$ | $C(CH_3)_3$ | H |
| $OCH_3$ | $CH_3$ | $C(CH_3)_3$ | H |
| H | H | $C(CH_3)_3$ | S-(Orn) |
| H | H | $C(CH_3)_3$ | S-(Val) |
| H | H | $C(CH_3)_3$ | S-(Lys) |
| H | H | $C(CH_3)_3$ | S-(Ala). |

3. An anti-malarial composition comprising a pharmaceutically effective amount of a ring substituted 8-aminoquinoline analog having a structure of formula 1,

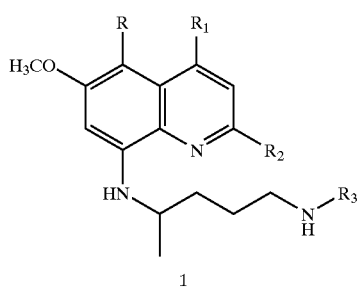

formula 1 wherein the R represents H, straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups; $R_1$ represents H, $CH_3$ and $C_2H_5$; $R_2$ represents straight chain alkyl group containing 1 to 5 carbons, branched alkyl groups, and cycloalkyl group containing 3 to 15 carbon atoms, and $R_3$ represents a (R)- or (S)-amino acid, an L-unnatural amino acid, or $R_3$ is H where (a) $R_1$ is H and $R_2$ is selected from the group consisting of $C(CH_3)_3$, 1-adamantyl, c-$C_5H_9$, $CH(CH_3)_2$, c-$C_6H_{11}$, and $C(CH_3)_3$, or (b) where $R_1$ is $CH_3$ or $C_2H_5$ and $R_2$ is $C(CH_3)_3$, and pharmacologically acceptable additive(s).

4. An anti-malarial composition as claimed in claim 3, wherein the pharmaceutically acceptable additive(s) are acceptable diluents selected from group consisting of lactose, mannitol, sorbitol, microcrystalline cellulose, sucrose, sodium citrate, and dicalcium phosphate; a binder selected from group consisting of gum tragacanth, gum acacia, methyl cellulose, gelatin, polyvinyl pyrrolidone, and starch; an excipient selected from group consisting of agar-agar, calcium carbonate, sodium carbonate, silicates, alginic acid, corn starch, potato tapioca starch, and primogel a lubricant selected from group of a magnesium stearate, calcium stearate or steorotes, talc, solid polyethylene glycols, ad sodium lauryl sulphate; a wetting agents selected from group consisting of acetyl alcohol, and glyceryl monostearate; an absorbent selected from group of kaolin, and bentonite clay; or a retarding agent selected from group consisting of wax, and paraffin, or a pharmaceutically acceptable flavor.

5. An anti-malarial composition as claimed in claim 3, wherein the value of R, R1, R2 and R3 of compound formula 1 are given below:

| R | $R_1$ | $R_2$ | $R_3$ |
|---|---|---|---|
| H | H | $C(CH_3)_3$ | H |
| c-$C_5H_9$ | H | H | H |
| H | H | 1-adamantyl | H |
| $CH(CH_3)_2$ | H | H | H |
| c-$C_6H_{11}$ | H | H | H |
| c-$C_5H_9$ | H | c-$C_5H_9$ | H |
| $CH(CH_3)_2$ | H | $CH(CH_3)_2$ | H |
| c-$C_6H_{11}$ | H | c-$C_6H_{11}$ | H |
| $OCH_3$ | H | $C(CH_3)_3$ | H |
| $OCH_3$ | H | c-$C_6H_{11}$ | H |
| $OCH_3$ | H | $CH(CH_3)_2$ | H |
| $OC_5H_{11}$ | $C_2H_5$ | $C(CH_3)_3$ | H |
| $OC_8H_{17}$ | $C_2H_5$ | $C(CH_3)_3$ | H |
| $OCH_3$ | $CH_3$ | $C(CH_3)_3$ | H |
| H | H | $C(CH_3)_3$ | S-(Orn) |
| H | H | $C(CH_3)_3$ | S-(Val) |
| H | H | $C(CH_3)_3$ | S-(Lys) |
| H | H | $C(CH_3)_3$ | S-(Ala). |

6. An anti-malarial composition as claimed in claim 3, wherein the $IC_{50}$ of the analog of formula 1 is about 39.06 ng/ml.

7. An anti-malarial composition as claimed in claim 3, wherein the analog of formula 1 is active against *P. berghei* infection at a dose ranging between 10–100 mg for about 4 days.

8. An anti-malarial composition as claimed in claim 3, wherein the $LD_{50}$ of the analog of formula 1 is about 400 mg per kg of body weight.

9. A composition as claimed in claim 3, wherein the composition is formulated in a form selected from the group consisting of a syrup, a tablet, a capsule, a powder, and a solution.

10. A process for preparation of a ring-substituted 8-aminoquinoline analog of formula 1

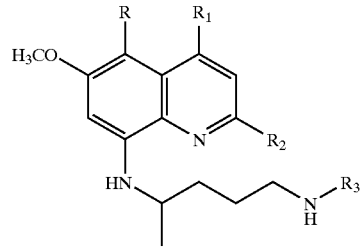

1 wherein R represents H, straight chain alkoxy groups containing 1 to 8 carbon atoms, branched chain alkyl groups containing 3 to 7 carbon atoms, cycloalkyl group containing 3 to 15 carbon atoms, phenoxy, and substituted phenoxy groups; $R_1$ represents H, $CH_3$ and $C_2H_5$; $R_2$ represents straight chain alkyl group containing 1 to 5 carbons, branched alkyl groups, and cycloalkyl group containing 3 to 15 carbon atoms and $R_3$ represents H, a (R)- or (S)-amino acid or an L-unnatural amino acid, and pharmacologically acceptable additive(s), wherein the salt-forming acid may be organic or inorganic in nature, said process comprises steps of:

reacting 8-nitroquinolines with alkyl carboxylic acid in presence of sulphuric acid, silver nitrate and ammonium persulphate in aprotic solvent at reflux temperature for a period in the range of 5 min to 1 hr to isolate the ring substituted 8-aminoquinoline from the reaction mixture;

reducing the ring-substituted 8-aminoquinoline obtained in step (a) with a catalyst and hydrogen under pressure to obtain ring-substitued 8-nitroquinoline;

reacting the obtained ring substituted 8-nitroquinoline with 2-(4-bromopentyl)-1,3-isoindolinedione and tryethylamine at a temperature ranging between 100–140° C. for a period in the range of 3–8 hrs to provide isoindolinedione derivative;

reacting the isoindolinedione derivative obtained in step (c) with hydrazine-hydrate in alcoholic solvent to produce ring substituted $N^8$-(4-amino-1-methylbutyl)-8-quinolinamine, and reacting $N^8$-(4-amino-1-methylbutyl)-8-quinolinamine obtained in step (d) with N-protected amino acid and dicyclohexylcarbodiimide in chloroalkane solvent at a temperature ranging between 10–50° C., isolating the ring substituted protective amino acid quinoline derivative followed by deprotection of amino acid moiety in the molecule to give compound of formula 1.

11. A process as claimed in claim 10, wherein the alkyl carboxylic acid is selected from a group consisting of tri-methyl acetic acid, isobutyric acid, cyclo-hexane carboxylic acid, and 1-adamantanecarboxylic acid.

12. A process as claimed in claim 10, wherein the 8-nitroquinoline is selected from the group consisting of 6-methoxy-8-nitroquinoline, 5,6-dimethoxy-8-nitroquinoline, 4-ethyl-5-pentoxy-6-methoxy-8-nitroquinoline, 4-ethyl-5-octoxy-6-methoxy-8-nitroquinoline, and 4-methyl-5,6-dimethoxy-8-nitroquinoline.

13. A process as claimed in claim 10, wherein reduction in step (b) employs raney-nickel.

14. A process as claimed in claim 10, wherein reduction in step (b) is carried out at a pressure in the range of 40–50 psi in a Parr hydrogenator.

15. A process as claimed in claim 10, wherein the alcoholic solvent is ethyl alcohol.

16. A process as claimed in claim 10, wherein the chloroalkane solvent is dichloro-methane.

17. A process as claimed claim in 10, wherein the deprotection of benzyl-esters in amino acid moiety in the molecule in step (e) is carried out in presence of Pd—C in methanol in presence of hydrogen gas.

18. A process as claimed in claim 10, wherein the deprotection of t-Boc protected amino acid is carried out in presence of methanolic HCl.

19. A process as claimed in claim 10, wherein the value of R, R1, R2 and R3 of formula 1 are given below:

| R | $R_1$ | $R_2$ | $R_3$ |
|---|---|---|---|
| H | H | $C(CH_3)_3$ | H |
| c-$C_5H_9$ | H | H | H |
| H | H | 1-adamantyl | H |
| $CH(CH_3)_2$ | H | H | H |
| c-$C_6H_{11}$ | H | H | H |
| c-$C_5H_9$ | H | c-$C_5H_9$ | H |
| $CH(CH_3)_2$ | H | $CH(CH_3)_2$ | H |
| c-$C_6H_{11}$ | H | c-$C_6H_{11}$ | H |
| $OCH_3$ | H | $C(CH_3)_3$ | H |
| $OCH_3$ | H | c-$C_6H_{11}$ | H |
| $OCH_3$ | H | $CH(CH_3)_2$ | H |
| $OC_5H_{11}$ | $C_2H_5$ | $C(CH_3)_3$ | H |
| $OC_8H_{17}$ | $C_2H_5$ | $C(CH_3)_3$ | H |
| $OCH_3$ | $CH_3$ | $C(CH_3)_3$ | H |
| H | H | $C(CH_3)_3$ | S-(Orn) |
| H | H | $C(CH_3)_3$ | S-(Val) |
| H | H | $C(CH_3)_3$ | S-(Lys) |
| H | H | $C(CH_3)_3$ | S-(Ala). |

20. A process as claimed in claim 10, wherein the analog of formula 1 is active against *P. berghei, P. yoelii* infection at a dose ranging between 10–100 mg for 4 days.

21. A process as claimed in claim 10, wherein the $LD_{50}$ of the analog of formula 1 is about 400 mg per kg of body weight.

22. A process as claimed in claim 10, wherein the ring substituted 8-aminoquinoline analog is free from methemoglobin (MetHb) toxicity.

23. A method of treating a subject in need thereof for malarial infection comprising a step of administering to the subject a pharmaceutically effective dosage of a compound according to claim 1 together with a pharmaceutically acceptable salt(s), carrier, or additive.

24. A method of treatment as claimed in claim 23, wherein the subject is a mammal.

25. A method of treatment as claimed in claim 23, wherein the compound of formula 1 is active against *P. berghei* and *P. yoelii* infection at a dose ranging between 10–100 mg for 4 days.

26. A method of treatment as claimed in claim 23, wherein the $LD_{50}$ of the compound of formula 1 is about 400 mg per kg of body weight.

27. A method of treatment as claimed in claim 23, wherein the said pharmaceutically effective dosage has a broad spectrum of anti-malarial activity against blood stages, tissue stages of malarial parasite.

28. A method of treatment as claimed in claim 23, wherein the said pharmaceutically effective dosage is effective against resistant strains of human malarial parasite.

* * * * *